US006532835B1

(12) United States Patent
Saaski et al.

(10) Patent No.: US 6,532,835 B1
(45) Date of Patent: Mar. 18, 2003

(54) HIGH EFFICIENCY WETTED SURFACE CYCLONIC AIR SAMPLER

(75) Inventors: Elric W. Saaski, Bothell, WA (US); Chuck C. Jung, Lynnwood, WA (US); David A. McCrae, Richmond, CA (US)

(73) Assignee: Research International, Inc., Woodinville, WA (US)

( * ) Notice: Subject to any disclaimer, the term of this patent is extended or adjusted under 35 U.S.C. 154(b) by 597 days.

(21) Appl. No.: 08/990,038

(22) Filed: Dec. 12, 1997

(51) Int. Cl.[7] .................................................. G01N 1/00

(52) U.S. Cl. .................................................. 73/863.21

(58) Field of Search ........................ 73/863.21; 96/243, 96/250, 265, 272, 301–308; 95/216

(56) References Cited

U.S. PATENT DOCUMENTS

| 2,768,705 A | * 10/1956 | Isserlis ........................ 96/308 |
| 2,847,083 A | * 8/1958 | Hibshman .................... 96/303 |
| 3,465,883 A | 9/1969 | Jumper |
| 3,791,777 A | 2/1974 | Papoff et al. ................ 417/475 |
| 3,926,592 A | 12/1975 | Leva ............................ 55/84 |

(List continued on next page.)

OTHER PUBLICATIONS

Air Sampling Instruments; American Conference Of Governmental Industrial Hygienists;1978; pp. K10–K12, K26–K27, M14–M15, P2–P15, R4–R5.
High Efficiency Sampler Design; Jul. 26, 1996; Saaski, Elric W.; vol. 1, pp. 3–29.
Fine Particles In Gaseous Media; Hesketh, Howard E.; 1986; pp. 109–155.
Industrial Gass Cleaning; Strauss, W.; 1975; pp. 216–276 and 367–408.
Numerical And Experimental Studies Of Particle Deposition In A Tube With A Conical Contraction–Laminar Flow Regime; Chen, Da–Ren et al.; J. Aerosol Sci., vol. 26, No. 4, pp. 563–574; 1995.
High Performance Portable Sampler; Saaski, Elric W.; Nov. 15, 1996; pp. 1–39.

(List continued on next page.)

*Primary Examiner*—Robert Raevis
(74) *Attorney, Agent, or Firm*—Gregory W. Moravan

(57) ABSTRACT

An air sampler having a fan; an air inlet tube; a main body having a cyclonic cup, a stripping column and a demister; and fluidic circuitry for inputting fluids to the main body and the air inlet tube, and for outputting fluids from the main body. Air flow through the air sampler may be generated by a fan that is either external or internal with respect to the main body's cyclonic cup. A thin film of stripping liquid and/or a fog of stripping liquid particles in the air inlet tube, the cyclonic cup, the stripping column and/or the demister strip a target material from the air flow through the air sampler. A passive fog generating slot or a passive spiral fog generating nozzle may be placed over the fluid input conduit in the center of the cyclonic cup. The air sampler's main body and/or an air inlet tube may be integrally formed as one part. The main body's inner surfaces may be selected to be hydrophilic, for better flow of the thin film of stripping liquid across them; and its intersecting internal surfaces may be provided with smoothly curved fillets for better air and liquid flow over them. The air sampler may be provided with a liquid level control that may have a reservoir float monitored by external optical sensors; a flexible, capacitive effect, dual electrode bearing substrate that is wrapped around the exterior of the air sampler's stripping column; or an external optical bubble sensor for the reservoir's output conduit. The air sampler may be so small, light and low in energy consumption that it may be battery powered and human-portable; and may be so efficient that it may be used to strip target material that is present in the incoming air in concentrations of only a few parts per trillion, or less.

67 Claims, 10 Drawing Sheets

U.S. PATENT DOCUMENTS

| | | | | |
|---|---|---|---|---|
| 4,002,127 | A | 1/1977 | Angus | 110/8 |
| 4,015,957 | A * | 4/1977 | Grantham | 96/265 |
| 4,286,973 | A | 9/1981 | Hamlin et al. | |
| 4,352,681 | A | 10/1982 | Dietz | |
| 4,409,274 | A | 10/1983 | Chaplin et al. | 428/112 |
| 4,482,347 | A | 11/1984 | Borsanyi | |
| 4,518,327 | A | 5/1985 | Hackman | |
| 4,545,745 | A | 10/1985 | Barreca | |
| 4,568,255 | A | 2/1986 | Lavender et al. | |
| 4,604,038 | A | 8/1986 | Belew | |
| 4,624,691 | A | 11/1986 | Schneider | |
| 4,652,520 | A | 3/1987 | Bauman | |
| 4,728,265 | A | 3/1988 | Cannon | |
| 4,869,880 | A | 9/1989 | Hettinger, Jr. et al. | |
| 4,921,150 | A | 5/1990 | Lagergren et al. | |
| 4,969,934 | A | 11/1990 | Kusik et al. | |
| 5,083,908 | A | 1/1992 | Gagnebin et al. | |
| 5,093,029 | A | 3/1992 | Husain et al. | |
| 5,126,043 | A | 6/1992 | Giordano et al. | |
| 5,173,038 | A | 12/1992 | Hopfensperger et al. | |
| 5,207,805 | A | 5/1993 | Kalen et al. | |
| 5,215,450 | A | 6/1993 | Tamari | |
| 5,326,236 | A | 7/1994 | Kramer et al. | |
| 5,333,511 | A | 8/1994 | Boyum et al. | |
| 5,357,726 | A | 10/1994 | Effenberger et al. | 52/309.7 |
| 5,380,173 | A | 1/1995 | Hellstrom | |
| 5,443,451 | A | 8/1995 | Chapman et al. | |
| 5,500,369 | A | 3/1996 | Kiplinger | |
| 5,688,112 | A | 11/1997 | Garay | |
| 5,705,018 | A | 1/1998 | Hartley | |
| 5,730,922 | A | 3/1998 | Babb et al. | 264/268 |
| 5,858,551 | A | 1/1999 | Salsman | 428/480 |
| 5,919,525 | A | 7/1999 | Appelt et al. | 427/379 |

OTHER PUBLICATIONS

Dielectrophoretic Air Filtration: Progress And Problems; Thompson, J.K., et al.; U.S. Naval Research Laboratory; pp. 361–372; exact date is unknown, but is believed to be earlier than 1995.

Novel Concepts, Methods And Advanced Technology In Particulate–Gas Separation; Ariman, Teoman; Apr. 20–22, 1977; Proceedings of the Workshop held at The Center For Continuing Education, University of Notre Dame, Notre Dame, Indiana, pp. 237–360.

* cited by examiner

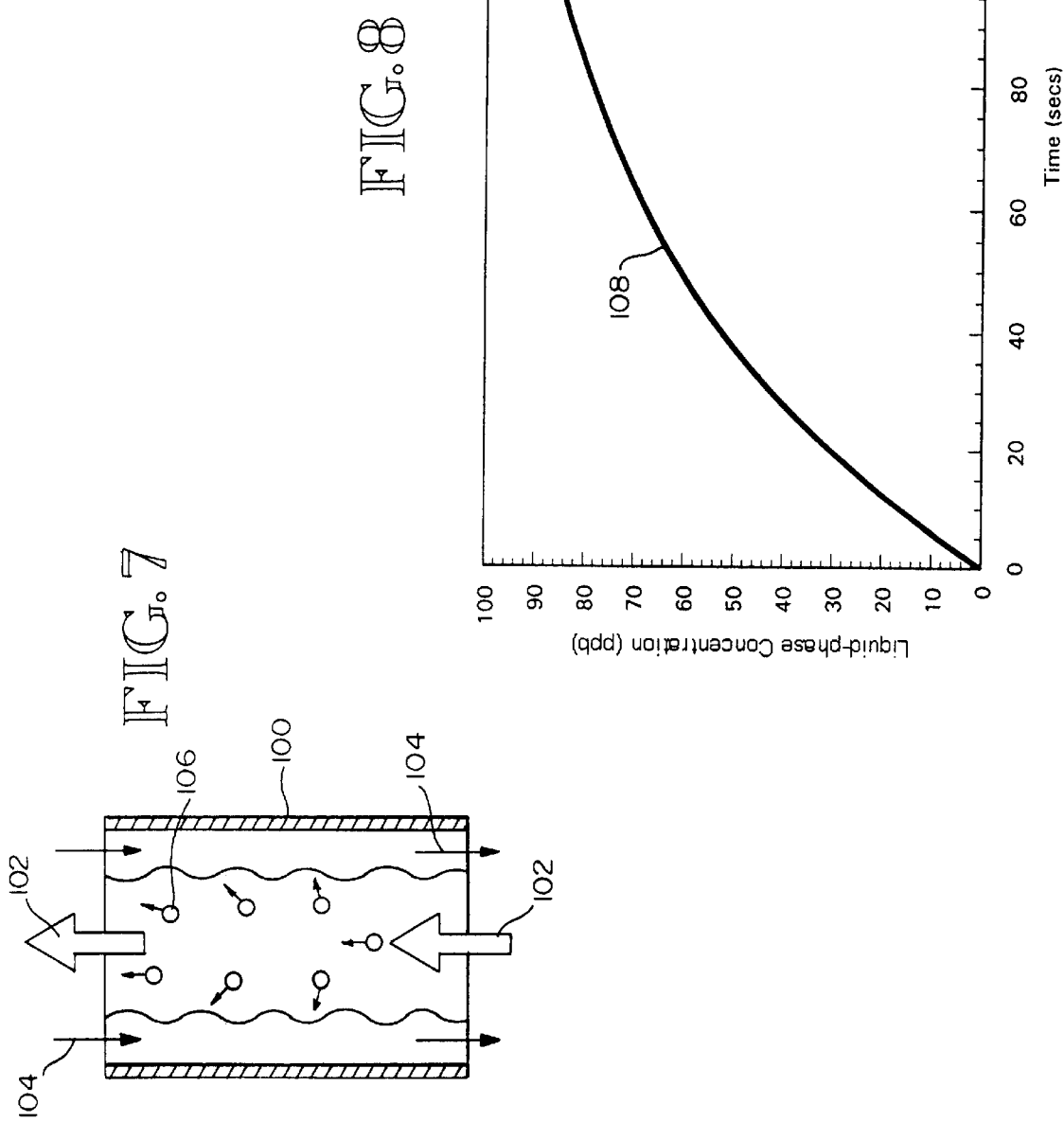

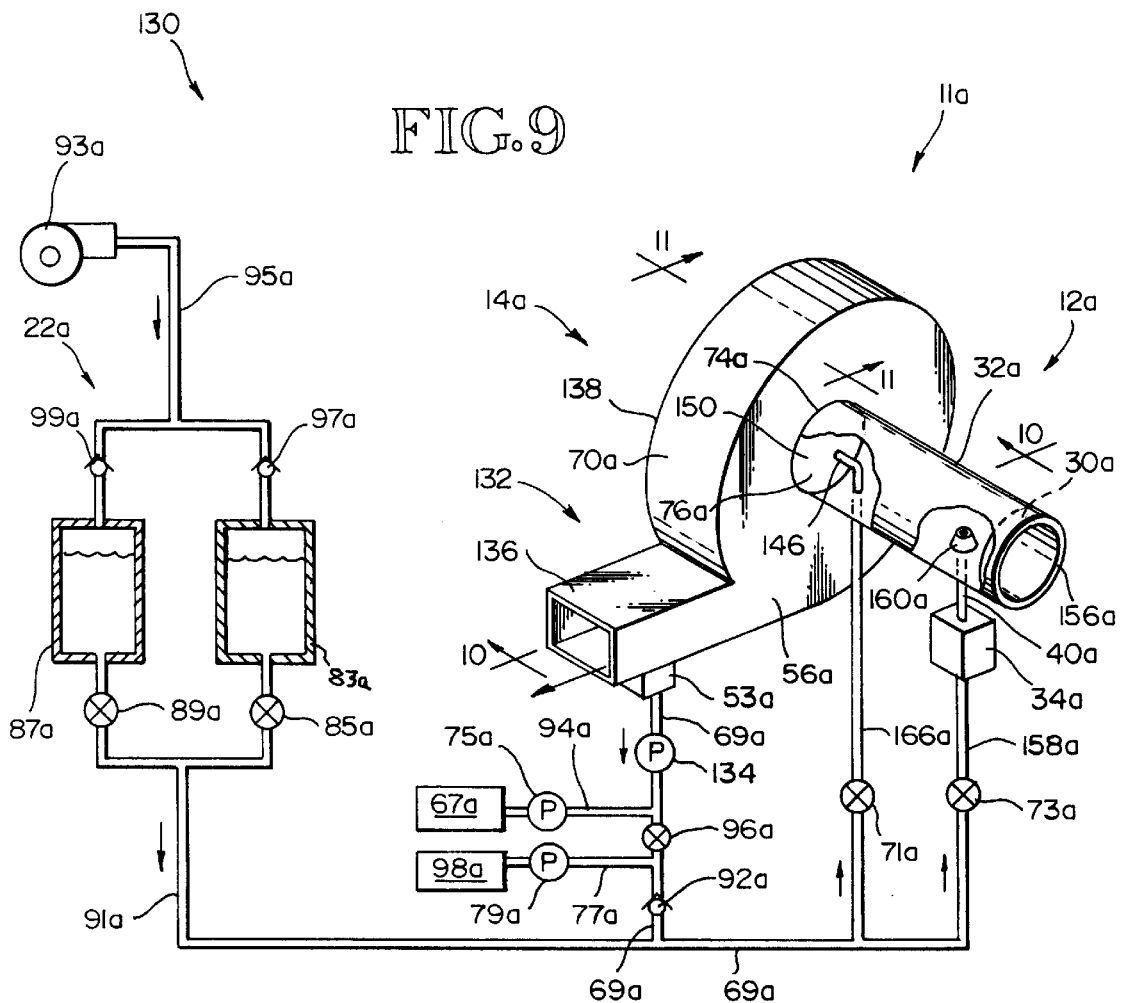

HIGH EFFICIENCY WETTED SURFACE CYCLONIC AIR SAMPLER

STATEMENT REGARDING FEDERALLY SPONSORED RESEARCH AND DEVELOPMENT

The U.S. Government may have a paid-up license in this invention and may have the right in limited circumstances to require the patent owner to license others on reasonable terms as provided for by the terms of Contract No. DABT63-97-C-0007 awarded by the Defense Advanced Research Projects Agency.

BACKGROUND OF THE INVENTION

The present invention relates to air samplers. More particularly, it relates to air samplers that strip a target material from the ambient air (the air mass being sampled), and concentrate it in a stripping liquid. The stripping liquid may then be delivered to any suitable detection apparatus for the target material.

SUMMARY OF THE INVENTION

One aspect of the present invention may be to provide a high efficiency wetted wall cyclonic air sampler that is so small, so light weight and so low in energy consumption that it may be battery powered and human-portable; and that is so efficient that it may be used to strip target material that is present in the ambient air in concentrations of only a few parts per trillion, or less.

The target material may comprise one or more solids, liquids and/or gasses. If the target material is a solid, it may comprise particulate matter such as dust, bacteria, or viruses, for example. If the target material is a liquid, the particulate matter may comprise liquid droplets, such as a mist or fog, for example. If the target material is a gas, it may comprise any gas-phase molecular species.

Another aspect of the present invention may be that the air flow through the air sampler's main body and air inlet section may be provided by a fan, such as when the air sampler is stationary or is moving at a relatively low velocity with respect to the ambient air. Air flow through the air sampler may also be provided by movement of the air sampler through the ambient air.

A first embodiment of the air sampler may comprise an air inlet section, a main body and a fan. If a fan is used, it may urge air through the air inlet section and the main body during use of the air sampler.

The air sampler's main body may comprise a cyclonic cup, a stripping column and a demister. Ambient air flows tangentially into the cyclonic cup's perimeter from the air inlet section, creating a rapidly rotating air flow within the cyclonic cup and an upwardly rising air vortex that extends from the cyclonic cup, through the stripping column and into the demister.

The low pressure area created by the air vortex in the center of the cyclonic cup may be used to permit, or assist, the stripping liquid to be gravity fed into the cyclonic cup through an input port in the center of cyclonic cup's base, with little or no external pump pressure for the stripping liquid being needed.

The shear forces generated by the upwardly rising air vortex within the cyclonic cup may urge the incoming stripping liquid to form around the cup's input port a thin film that flows radially outwardly across the cyclonic cup's base, that then flows in a spiral path up the inner surface of the cyclonic cup's sidewalls, and that then flows onto the inner surface of the stripping column.

Similarly, the shear forces generated by the upwardly rising air vortex within the stripping column may urge the stripping liquid from the cyclonic cup to form a thin film that flows in a spiral path up the inner surface of the stripping column, and that then flows across the top edge of the stripping column; to fall into the demister's reservoir under the force of gravity.

From the reservoir, the stripping liquid may be recycled one or more times by gravity feed back to the input port in the cyclonic cup, so that it may pass through the cyclonic cup, the stripping column and the demister again; to strip still more target material from the air passing through the air sampler. A liquid level control may be provided for the reservoir.

Thus, the cyclonic cup, the stripping column and the demister may be "self-pumping", in the sense that no external liquid pump may be needed to force the stripping liquid through them, since that job may be done by the action of the air/liquid shear forces generated by the upwardly rising air vortex within them; and since no external liquid pump may be needed to recirculate the stripping liquid from the demister's reservoir back into the cyclonic cup, since that job may be done by gravity feed.

All along its journey from the cyclonic cup's input port to the demister's reservoir, the thin film of stripping liquid may strip the target material from the upwardly rising air vortex at high efficiencies. Such high efficiencies may be due to such factors as the high velocity of the circulating air and the upwardly rising air vortex; the very large surface area of the thin film; the very long path followed by the thin film as it flows across the cyclonic cup's base and spirals up the inside of the inner surfaces of the sidewalls of the cyclonic cup and the stripping column; the very low volume of stripping liquid that resides in the air sampler's main body and air inlet section at any one time; the very low flow rate of the stripping liquid through the air sampler's main body and air inlet section; the very high volume of air flowing through the air sampler; and/or the evaporation of substantial amounts of the stripping liquid by the air flowing through the air sampler.

The internal diameter of the stripping column may be less than that of the cyclonic cup, to cause the air vortex within the stripping column to rotate at a higher speed as compared to the air vortex in the cyclonic cup. The higher speed of rotation may help the stripping column to more effectively strip liquid and solid particulate target material from the air due to higher centrifugal forces; and may create a relatively lower pressure within the stripping column that may permit the relatively higher pressure within the cyclonic cup to urge the stripping liquid from the inner surface of the cyclonic cup to the inner surface of the stripping column.

The inner surface of the stripping column may be provided with spiral grooves for increasing its surface area; for providing a long spiral path for the thin film of stripping liquid to follow on its inner surface; and/or for helping to prevent air-entrainment of the stripping liquid on its inner surface by encouraging the air flow to follow a spiral path, by shielding the stripping liquid from the air flow's axially-directed shear forces, by preventing the stripping liquid from forming large surface waves that may be captured and subsequently broken into droplets by the air flow, and by providing a partially-protected path by which the stripping liquid can spill into the demister.

A portion of the stripping column may extend into the demister, and the diameter of the demister may be greater than the diameter of the stripping column, to provide a space between the larger sidewall of the demister and the smaller sidewall of the stripping column that may serve as the demister reservoir, and to reduce the speed of rotation and upward velocity of the air vortex within the demister to the point that at least some of any air-entrained stripping liquid may be dropped by the air vortex in the demister.

The air sampler's cyclonic cup may further comprise a passive (i.e., non-powered or non-moving) means for producing a fog of stripping liquid droplets that utilizes the low pressure area created in the center of the cyclonic cup by the cyclonic cup's air vortex, and that utilizes the extremely high tangential air velocities that may be created by the cyclonic cup's air vortex near the cyclonic cup's longitudinal axis.

A first embodiment of the passive fog generating means may comprise a radially oriented slot centered in the cyclonic cup's base that is fed by the cyclonic cup's stripping liquid input port. A second embodiment of the passive fog generating means may comprise a spiral fog generating nozzle having an input port located over the cyclonic cup's stripping liquid input port. With both embodiments of the passive fog generating means, the fog particles they produce may, during their passage through the cyclonic cup, the stripping column and the demister, strip the target material from the air and be deposited on the inner surfaces of the cyclonic cup, the stripping column and the demister. The fog particles that are deposited on the inner surfaces of the cyclonic cup and the stripping column may then become part of, and travel along with, the stripping liquid film on those surfaces. Any fog particles deposited on the inner surface of the demister's sidewall may drain, under the force of gravity, into the demister's reservoir. The extremely high efficiency with which the fog particles may strip the target material from the air may be due to such factors as their extremely small size, their extremely large numbers, and/or their extremely large cumulative surface area.

The air sampler's air inlet section may comprise an air inlet tube and a fog generator for producing a fog of stripping liquid droplets in the air inlet tube and/or in the cyclonic cup. During their passage through the air inlet tube, the cyclonic cup, the stripping column and the demister, the fog particles may strip the target material from the air and be deposited on the inner surfaces of the cyclonic cup, the stripping column and the demister. Those fog particles deposited on the inner surfaces of the cyclonic cup and the stripping column may then become part of, and travel along with, the stripping liquid film on those surfaces. Those fog particles deposited on the inner surface of the demister's sidewall may drain, under the force of gravity, into the demister's reservoir.

From all of the forgoing, it may now be seen that the air sampler's main body 11 and air inlet section 12 may provide a unique five-step stripping process for stripping the target material from the incoming air, namely, (a) the action of the fog of stripping liquid particles produced by the fog generator in the air inlet tube, (b) the action of the fog of stripping liquid particles produced by the fog generating means in the cyclonic cup, (c) the action of the film of stripping liquid on the inner surface of the cyclonic cup, (d) the action of the film of stripping liquid on the inner surface of the stripping column, and/or (e) the action of the film of stripping liquid on the inner surface of the demister.

A second embodiment of the cyclonic air sampler of the present invention may comprise a main body and/or an air inlet that may be formed as one integral piece, such as by blow-molding or roto-molding. The integrally formed main body and/or air inlet may have exceedingly smooth inner surfaces, and may have inner surfaces that intersect in smoothly curved fillets, for better flow of the air and/or thin water film over them, and to prevent the formation of undesirable water traps that may be hard to clean and that may cause the air sampler to produce erroneous readings regarding the target material under certain circumstances.

The second embodiment of the cyclonic air sampler may include external capacitive or optical liquid level controls that may inherently avoid any cleaning or clogging problems, since they may never be in direct contact with the liquids passing through the air sampler.

A third embodiment of the cyclonic air sampler of the present invention may comprise an air inlet section, a main body and an air outlet section. Its main body may comprise a cyclonic cup having an internal, high speed, radial flow air impeller. Stripping liquid fed into the air inlet section may be urged by the spinning impeller to form a thin film on the impeller's inner surfaces. The spinning impeller may then urge the thin film to move across the impeller's inner surfaces to the impeller's peripheral air outlet, where it may then be flung onto the cyclonic cup's end wall to form a thin film on the cyclonic cup's end wall. The air flow from the impeller through the cyclonic cup's air chamber may then urge the thin film on the cyclonic cup's end wall to enter a reservoir in the air outlet section. The thin film on the impeller's inner surfaces and the cyclonic cup's end wall may strip the target material from the air. The liquid from the reservoir may be recycled back into the air inlet section to strip more target material from the air.

The third embodiment's air inlet section may comprise an air inlet tube and a fog generating means for producing a fog of stripping liquid particles in the air inlet tube. During their passage through the air inlet tube, the air chambers within the impeller, and the cyclonic cup's air chamber, the fog particles may strip the target material from the air and be deposited on the inner surfaces of the air impeller and the cyclonic cup's end wall. Those fog particles deposited on the inner surfaces of the air impeller and the cyclonic cup's end wall may then become part of, and travel along with, the stripping liquid film on those surfaces.

The cyclonic cup's end wall may be enlarged and/or may have a concave cross-sectional configuration, to increase its surface area, and to thus increase the surface area of the thin film of stripping liquid that it may carry.

The third embodiment may be highly efficient at stripping the target material from the air for reasons which are at least similar to, if not the same as, those set forth above regarding the first and second embodiments of the air sampler.

The inner surfaces of any of the embodiments of the air sampler that are wetted by the stripping liquid may be made from a hydrophilic material, may be coated with a hydrophilic material and/or may be treated to become hydrophilic, to improve their wettability and the thinness of the film of stripping liquid they may carry.

As used herein, the terms "wetted", "wettable", "wettability", "hydrophilic", "hydrophobic", and the like, are to be interpreted as having meanings with respect to non-aqueous stripping liquids that correspond to their meanings when used with aqueous stripping liquids.

Air entering any of the embodiments of the air sampler may comprise air that is received directly from the ambient air; and/or it may comprise the output of a preconcentrator that receives the ambient air and provides a steady or pulsatile output stream of air that is already enriched with the target material. A suitable preconcentrator may also comprise means for removing large, non-target material debris from the air passing through it, such as a dry air cyclone or a canister with an absorbent material.

Any of the embodiments of the air sampler may further comprise fluidic circuitry that may be designed for multiple functions such as, for example, supplying the air sampler's main body and/or air inlet section with stripping liquid and/or cleaning liquid; removing waste liquid from the air sampler's main body and/or air outlet section; removing samples of the stripping liquid (which may contain stripped target material) from the air sampler's main body and/or air outlet section; and/or detecting the presence, amount and/or identity of the target material in the samples of the stripping liquid.

The fluidic circuitry may further comprise a novel dual roller peristaltic sample and/or waste pump. The peristaltic pump may act as a normally-closed valve when shut off, may consume a very small amount of electric power due to its innovative design, and may be long-lived, self-priming, easily cleaned, light-weight, insensitive to shock, and/or computer-controllable.

It should be understood that the foregoing summary of the present invention does not set forth all of its features, advantages, characteristics, structures, methods and/or processes; since these and further features, advantages, characteristics, structures, methods and/or processes of the present invention will be directly or inherently disclosed to those skilled in the art to which it pertains by all of the disclosures herein.

BRIEF DESCRIPTION OF THE FIGURES

FIG. 7 is a cross-sectional view of a theoretical model for certain aspects of the air sampler 10;

FIG. 8 is a graph illustrating certain features of the model of FIG. 7;

FIG. 9 is a diagrammatic view, partly in perspective, partly in cross-section and partly in elevation, of the high efficiency, wetted surface, cyclonic air sampler 130 of the present invention;

DESCRIPTION OF THE PREFERRED EMBODIMENTS

THE HIGH EFFICIENCY, WETTED SURFACE, CYCLONIC AIR SAMPLER 10

Figure 1:
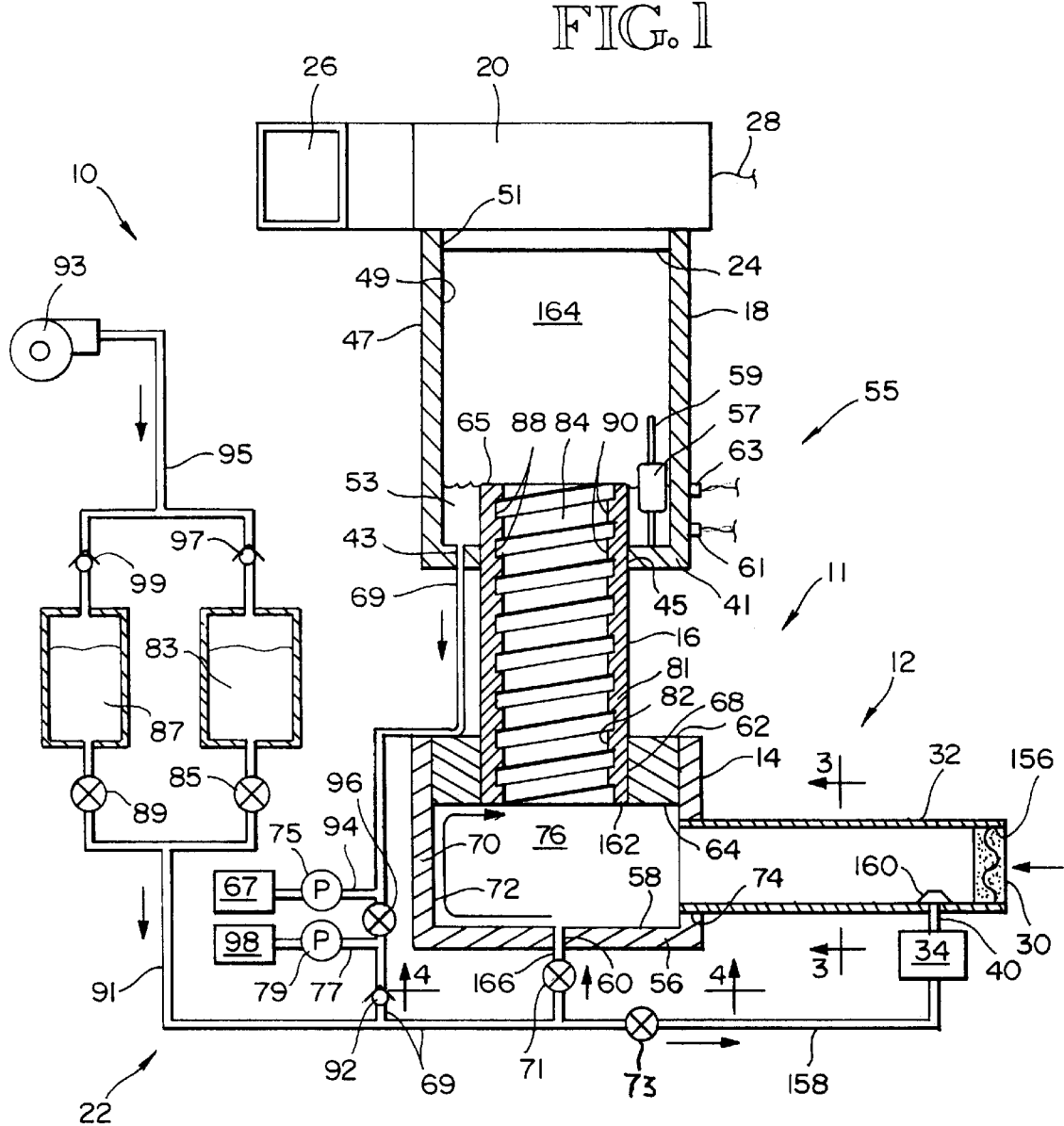
FIG. 1 is a diagrammatic view, partly in elevation and partly in cross-section, of the high efficiency, wetted surface, cyclonic air sampler 10 of the present invention.

Turning now to FIG. 1, the high efficiency, wetted surface, cyclonic air sampler 10 of the present invention may comprise an a main body 11; an air inlet section 12; and a fan 20 for urging air through the main body 11 and/or the air inlet section 12. The air sampler 10 may further comprise fluidic circuitry 22. As will be described below in detail, the fluidic circuitry 22 may be designed for multiple functions such as, for example, supplying stripping liquid to the main body 11 and/or the air inlet section 12; supplying cleaning liquid to the main body 11 and/or the air inlet section 12; removing waste liquid from the main body 11; removing samples of the stripping liquid (which may contain stripped target material) from the main body 11; and/or detecting the presence, amount and/or identity of the target material in the samples of the stripping liquid.

The air sampler 10's air inlet section 12 may comprise an air inlet tube 32, an air filter 30 and a fog generator 34. Its main body 11 may comprise a cyclonic cup 14, a target material stripping column 16, and a demister 18.

The target material may be in the form of particles, which may be in either liquid or solid form. The target material also may be in the form of a vapor. As used herein, the term vapor includes any gas, but does not include liquids or solids.

In the description which follows, water will be the stripping liquid employed in the air sampler's main body 11 and/or air inlet section 12 to strip the target material from the incoming air. However, water is being employed only by way of example. It is understood that any other suitable stripping liquid may be used, depending on such factors as the specific target material that is to be stripped from the incoming air, and the environment in which the air sampler 10 is to be used. For example, if the target material is to be dissolved in the stripping liquid, but the target material is not soluble in water, or is only slightly soluble in water, then the water may be replaced by any suitable stripping liquid in which the target material is highly soluble.

In general, the relatively high air flow through the air sampler's main body 11 and/or air inlet section 12 may have the desirable effect of increasing the concentration of the target material in the water, due to the relatively large amount of the water that may be evaporated by the air flow while the water is passing through the air sampler's main body 11 and/or air inlet section 12. To aid in such an evaporation-concentration effect, the stripping liquid may comprise liquids having a volatility substantially greater than that of water, such as an alcohol or other organic liquid.

As used herein, the term "air" is not limited to atmospheric air, but may include any gas or mixture of gases.

THE FAN 20:

The fan 20 may be any suitable conventional radial or axial flow fan, and may have an inlet 24, and outlet 26 and receive electrical power through an electrical cord 28. The fan's inlet 24 may be mounted in the demister 18's air outlet 51. During operation of the air sampler 10, the fan 20 may pull air through the air inlet section 12 and the main body 11 (i.e., may pull air sequentially through the air inlet tube 32, the cyclonic cup 14, the stripping column 16 and the demister 18), before exhausting the air out through the fan 20's outlet 26.

Alternatively, the fan 20 may be located so that its outlet 26 may force air into the air inlet tube 32's inlet 156. In such an event, the air filter 30 may be located either over the fan 20's inlet 24 or in the air inlet tube 32. The air from the fan 20 may pass sequentially through the air inlet tube 32, the cyclonic cup 14, the target material stripping column 16 and the demister 18, before exiting the main body 11 through the demister 18's air outlet 51.

Alternatively, the fan 20 may be eliminated, and air may be forced into the air inlet tube 32 by the ram air effect generated by relative motion between the air inlet tube's air inlet 156 and the surrounding air, such as if the air sampler 10 were carried by an airplane or other moving vehicle. Such a ram air effect may be enhanced by enlarging the air inlet 156 to form an air scoop having an intake larger in cross section than the air inlet tube 32.

Such an air scoop type air inlet 156 may permit the air sampler 10 to be used at lower relative speeds between the air inlet tube 32 and the surrounding air than might otherwise be the case, since an air scoop type air inlet 156 may collect relatively large amounts of relatively low velocity air due to an increased pressure difference at the air scoop type air inlet 156.

THE AIR FILTER 30:

The air filter 30 in the air inlet tube 32 may be any suitable conventional air filter, and may selected to filter out non-target material debris from the main body 11's incoming airstream that is larger than the largest particles of the target material that are to be stripped from the air by the main body 11. On the other hand, if the target material is in the form of a vapor, then the air filter 30 may be selected to filter out debris that is at least as small as the smallest opening in the main body 11 and in the possibly affected parts of the fluidic circuitry 22, in order to help prevent the debris from clogging the main body 11 and the possibly affected parts of the fluidic circuitry 22.

Alternatively, the air filter 30 may be optional, such as where the incoming air for the air inlet 156 is already relatively free from debris, which may be the case when the air sampler 10 is carried by an aircraft, for example; or which may be the case where the incoming air for the air inlet 156 is being provided by a preconcentrator which has already removed debris.

The Air Inlet Tube 32 and the Fog Generator 34:

The fog generator 34 may be optional, such as if the water needed to strip the target material from the air is fed directly into the cyclonic cup 14 through its input port 60, as will be described below in detail by way of example. If the fog generator 34 is eliminated, then the air inlet tube 32 may also be eliminated, and the air filter 30 may be placed directly over the cyclonic cup 14's air inlet 74.

However, if a fog generator 34 is used, in order to permit the water fog particles 54 that are emitted from the nozzle 160 of the fog generator 34 to strip as much of the target material from the air in the air inlet tube 32 as may be reasonably possible, the cross-sectional area of the air inlet tube 32, the quantity and size of water fog particles 54 emitted by the nozzle 160, and/or the location and/or orientation of the nozzle 160 within the air inlet tube 32 may be selected so that for any desired velocity of the incoming air, the entire air inlet tube 32 downstream from the nozzle 160, and the cyclonic cup 14, may be filled with the water fog particles 54 during operation of the air sampler 10 at any suitable volume fraction, such as a volume fraction in the range of about $10^{-6}$ to $10^{-4}$ parts water per unit volume of air/water mixture, for example.

In this regard, a suitable location for the nozzle 160 of the fog generator 34 may be just inside the air inlet tube 32's sidewall, with the nozzle 160 being oriented to point radially inwardly, to permit the nozzle 160 to inject the water fog particles 54 radially inwardly into the air inlet tube 32. Another suitable location for the nozzle 160 may be on the longitudinal centerline of the air inlet tube 32, with the nozzle 160 also being oriented to point along the longitudinal centerline, to permit the nozzle 160 to inject the water fog particles 54 into the central portion of the air inlet tube 32 either upstream or downstream with respect to the incoming air.

In addition, in order to help ensure thorough mixing of the water fog particles 54 with the incoming air, the air inlet tube 32 may be provided with any suitable means for preventing or destroying laminar air flow within the air inlet tube 32 (i.e., for adding turbulence to air flow within the air inlet tube 32), either upstream or downstream from the nozzle 160. For example, a small plate having a diameter smaller than the internal diameter of the air inlet tube 32 may be mounted in the center of the air inlet tube 32, perpendicular to the longitudinal centerline of the air inlet tube 32, and just upstream from the nozzle 160. Alternatively, the air inlet tube 32 may be provided with one or more vanes located, sized, and arranged to cause the air to swirl within the air inlet tube 32.

Further, for any desired velocity of the incoming air, the length of the air inlet tube 32 may be selected to permit the water fog particles 54 to have adequate time to strip as much of the target material from the air as may be reasonably possible; keeping in mind that the target material may also be stripped from the air by the cyclonic cup 14, the stripping column 16 and the demister 18, and keeping in mind the minimum time desired for the detection equipment (that may receive the target material laden water from the air sampler's main body 11), to detect the presence, amount and/or identity of the target material.

In addition, in order to help prevent the water fog particles 54 from coalescing on the inside of the air inlet tube 32 (which may dramatically reduce their effectiveness in stripping the target material from the air), the air inlet tube 32 may either be made from, or have its inner surface coated with, any suitable hydrophobic material such as teflon, polypropylene or polyethylene, for example.

As an alternative, the fog generator 34 may replace the cyclonic cup 14's input port 60 by being mounted so that its nozzle 160 is located at the bottom center of the cyclonic cup 14, and so that its nozzle 160 at least partially protrudes into the cyclonic cup 14's air chamber 76. In such an event, the air inlet tube 32 may still be kept, since it may help to properly guide incoming air into the cyclonic cup 14; but the air inlet tube 32 may be eliminated, if desired.

Figure 2:
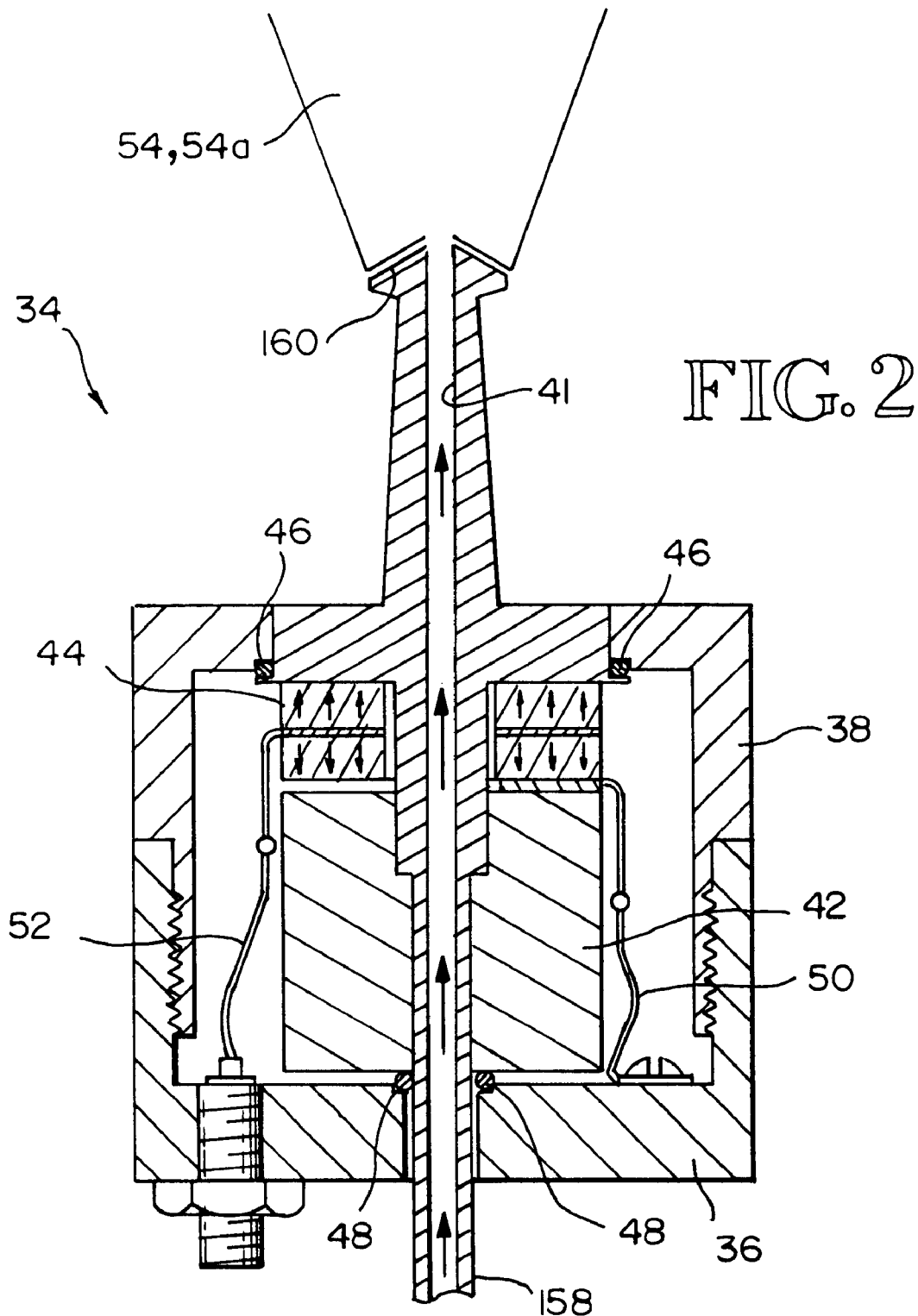
FIG. 2 is a diagrammatic cross-sectional view of a fog generator 34 that may be used in the air sampler 10.

Turning now to FIG. 2, the fog generator 34 may be any suitable conventional fog generator, such as a conventional piezoelectric ultrasonic fog generator comprising a base 36; a cover 38; an acoustic horn 40 having a bore 41 and a nozzle 160; a resonator 42; a piezoelectric actuator 44; a pair of elastomeric mounts 46, 48 that may comprise O-rings; and a pair of electrical leads 50, 52.

The cover 36 may be screwed to the base 34; the resonator 44 may be secured to the acoustic horn 40; the actuator 44 may be secured to the acoustic horn 40 and/or to the resonator 42; the acoustic horn 40 may be connected in any suitable way to the input conduit 158; and the electrical leads 50, 52 may be connected in any suitable way to an electrical power source.

During operation of the ultrasonic fog generator 34, an alternating electrical field may be applied to the piezoelectric actuator 44 by the electrical leads 50, 52 and by their associated field plates (not illustrated, for clarity). The alternating electrical field causes the actuator 44, and thus the acoustic horn 40 and its nozzle 160, to vibrate back and forth in directions that are parallel to the acoustic horn 40's longitudinal axis.

As the nozzle 160 moves back, the film of water that covers the exterior face of the nozzle 160 cannot move with the rapidity needed to match the nozzle 160's motion, causing the film of water to be literally suspended in air as the nozzle 160 moves back. The suspended film of water is unstable, and breaks into the desired fog of water particles 54. When the nozzle 160 then moves forward, an air cushion is created over the nozzle 160's exterior face that gently pushes the water fog particles 54 away from the nozzle 160.

The frequency of the electrical field applied to the actuator 44 may be in the range of about 40 kHz (kiloHertz) to about 2 MHz (megahertz). Relatively uniform-sized water fog particles 54 may be produced at any particular frequency, with their size being inversely proportional to the frequency of the applied electrical field. For example, at frequencies of about 40–80 kHz, the diameter of the uniform-sized water fog particles 54 may be in the range of about 20 to 40 microns, while at frequencies exceeding about 1 MHz, their diameter may be in the range of about 1–2 microns. Thus, an ultrasonic fog generator 34 offers the advantage of producing relatively uniform-sized water fog particles 54 having any desired size, within reason, by simply adjusting the frequency of the applied electrical field.

An ultrasonic fog generator 34 may also offer several other advantages over other types of fog generators, such as those relying on a restricted bore (typically less than about 0.254 mm (millimeters) in diameter), through which water is sprayed at a very high pressure (typically several hundred psi (pounds per square inch)), in order to produce the water fog particles 54. This is because an ultrasonic fog generator 34 may typically have a bore 41 that may be in the range of about 0.5–2.5 mm in diameter, and may typically have a feed pressure of about one psi, or less. Accordingly, an ultrasonic fog generator 34 may also offer such advantages as: simplicity; low weight; low power consumption; suitability for being gravity fed the water needed to produce the water fog particles 54, since no high pressure pumps are needed; and resistance to fouling, since its bore 41 may be relatively large.

As an alternative to using an ultrasonic fog generator 34 having a piezoelectric actuator 44, one having a magnetostrictive actuator 44 may be used. A magnetostrictive actuator 44 may comprise a magnetostrictive material that shrinks substantially when a magnetic field is applied to it, such as the magnetic field generated by current flow through a coil of wire surrounding the magnetostrictive material. By providing an alternating electrical current to the coil of wire, the magnetostrictive actuator 44 may be forced to vibrate in the manner described above regarding the piezoelectric actuator 44. A suitable magnetostrictive material may be the metal alloy Terfenol-D, manufactured by Etrema Products, Inc. of Ames, Iowa.

Alternatively, any other suitable type of conventional fog generating means, whether ultrasonic or not, may be used to produce the desired water fog particles 54 for the air sampler 10.

THE PASSIVE FOG GENERATING SLOT 168 AND THE PASSIVE FOG GENERATING SPIRAL NOZZLE 170:

It has been discovered that even certain passive (i.e., non-powered or non-moving) fog generating means may be used to produce the desired water fog particles 54 for the air sampler 10. This is because it may be shown on theoretical grounds that extremely high tangential air velocities may be found near the cyclonic cup 14's longitudinal axis, due to the air entering the cyclonic cup 14 at a tangent through its air inlet 74 (see FIGS. 3–4), and being extracted from the cyclonic cup 14 via a relatively small on-axis tube, namely the stripping column 16. This creates high surface shear forces near the center of the cyclonic cup 14's base 58; that may be used to atomize the water entering the cyclonic cup 14 through its input port 60.

Figure 5:
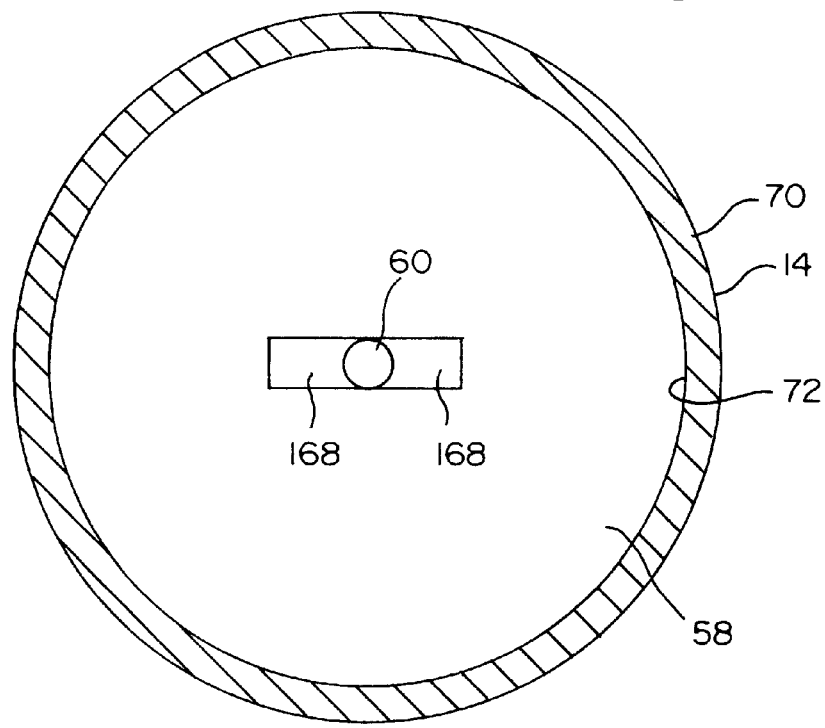
FIG. 5 is a top elevational view of the cyclonic cup 14's base 56 illustrating a first embodiment of a passive fog generating means, namely a fog generating slot 168.

One passive fog generating means for producing the desired water fog particles 54 for the air sampler 10 may comprise a passive, fog generating slot 168 which is best seen in FIG. 5. During operation of the air sampler 10, the slot 168 will first fill with water delivered to it by the input port 60. Then, as the water in the slot 168 attempts to rise and pool above the surface of the base 58 of the cyclonic cup 14, the high tangential air velocity of the air vortex within the cyclonic cup 14 will atomize the water by shearing fine droplets from the water along the edges of the slot 168.

Although the slot 168 is illustrated as being centered on the input port 60, it may be off center with respect to the input port 60. Although the slot 168 is illustrated as being radially oriented with respect to the input port 60, it may have any other suitable orientation with respect to the input port 60. Although the slot 168 is illustrated as being straight, it may follow a non-linear course. In addition, the length of the slot 168 may be longer or shorter than that illustrated; its depth may be shallower or deeper than that illustrated; and its depth and/or width may not be uniform along its length.

In general, the length, depth, shape and orientation of the slot 168 may depend on such factors as the viscosity of the stripping liquid, the diameter of the cyclonic cup 14, the rate of the air flow through the cyclonic cup 14, and the velocity of the air rotating within the cyclonic cup 14. In any event, the slot 168 may not be so narrow that the water's surface tension forces are so great that they prevent effective liquid shear; and the slot 168 may not be so wide that waves are produced by the air vortex that result in big, ineffective droplets when the waves are broken up by the air vortex.

By way of example, let it be assumed that the diameter of the cyclonic cup 14 is about 5.1 cm (centimeters); that the air flow rate though the cyclonic cup 14 is about 4.2 liters/sec; and that the air has a rotational velocity in excess of 1 m/sec (meters per second) at a radial distance of about 1 cm from the center of the cyclonic cup 14. For such an air sampler 10, the slot 168 seen in FIG. 5 may have a length of about 1 cm, a width in the range of about 0.75 to 3 mm, and a depth in the range of about 1.2 to 12 mm.

It has also been discovered that certain nozzle structures may be mounted over the input port 60 of the cyclonic cup 14 to provide the desired water fog particles 54 within the cyclonic cup 14.

In general, if the water is being fed from the reservoir 53 to the input port 60 by gravity feed and/or by the low pressure area within the center of the cyclonic cup 14 caused by the air vortex within it, the driving pressure difference for water flow into the port 60 may be quite small, on the order of about 10 mm of water, or less than 0.02 psig (pounds per square inch gauge), since it is governed by the vertical distance between the reservoir 53 and the input port 60, by the corresponding hydrostatic head of the water, and by the air-side pressure drop between the reservoir 53 and the low pressure area in the cyclonic cup 14. Thus, acceptable nozzle structures may need to have an open, low pressure drop internal structure that simultaneously allows: (a) free flow of the water through it; and (b) free exposure of the film of water on the exposed surfaces of the nozzle structure to the air flowing within the cyclonic cup 14, to enable that air flow to easily atomize the thin film of water.

Figure 6:
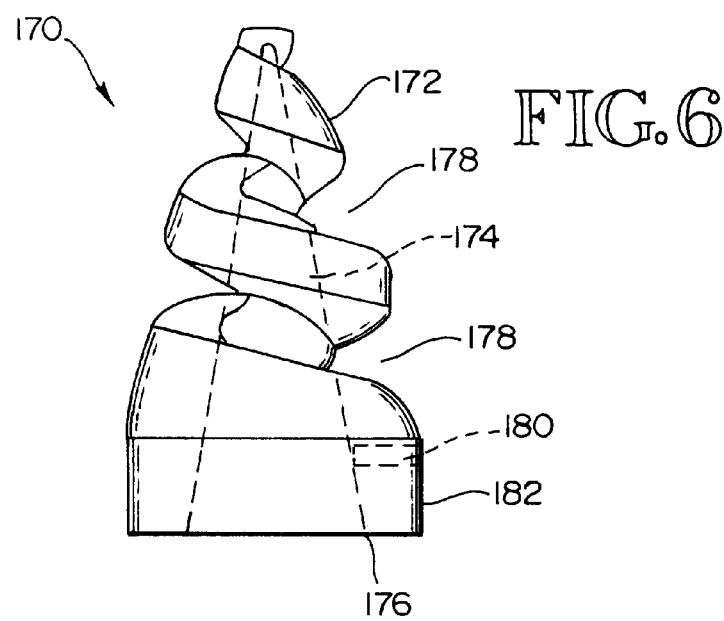
FIG. 6 is a side elevational view, partly in cross section, of a second embodiment of a passive fog generating means, namely a spiral fog generating nozzle 170.

For example, the spiral fog producing nozzle 170 illustrated in FIG. 6 is a conventional, model TF14FC fog nozzle made by Bete Fog Nozzle Inc. of Greenfield, Massachusetts, and normally requires at least about 10 psi of liquid pressure to produce a liquid fog. It has been discovered that the Bete fog nozzle 170 may also produce acceptable water fog particles 54 in the cyclonic cup 14, despite its liquid input pressure being only on the order of about 0.02 psig.

As seen in FIG. 6, the nozzle 170 may comprise a tapered, spiral body 172 having a tapered axial bore 174. The bore 174 may have an inlet 176, and a long, spiral outlet 178 that is provided between the several turns of the spiral body 172. The nozzle 170 may also be provided with a radial bore 180 in the nozzle 170's base 182 for providing fluid communication between the exterior of the nozzle 170 and its tapered axial bore 174.

Such a nozzle 170 may be secured with its inlet 176 located over the input port 60 of the cyclonic cup 14. Although not illustrated in FIG. 1, for clarity, the bottom of the cyclonic cup 14's base 58 may be provided with a cylindrical nozzle recess having a diameter slightly greater than the diameter the nozzle 170's base 182. The nozzle recess may also have a depth that is selected such that when the nozzle 170 is mounted in the nozzle recess, the bottom of its radial bore 182 will be about coplanar with the top surface of the cyclonic cup 14's base 58; to enable the radial bore 182 and the bottom portion of the axial bore 174 to drain into the input port 60 any water that might otherwise tend to accumulate in the bottom of the cyclonic cup 14, such as when the air sampler 10 is turned off.

The spiral fog nozzle 170 may be desirable because: (a) it may have a very low liquid pressure drop and be resistant to clogging, due to the large sizes of its inlet 176 and its spiral outlet 178; (b) its spiral body 172 has a very large exposed surface area, all of may be easily coated with a thin film of the incoming water, which may then simultaneously be easily acted upon (and atomized) by the shear forces of the rapidly rotating air vortex in the cyclonic cup 14; and (c) the vertically elongated nature of its spiral body 172 may permit the rapidly rotating air vortex in the cyclonic cup 14 to act on (and atomize) the thin film of water on the spiral body 172 at all elevations covered by the spiral body 172, rather than only at the cyclonic cup 14's base 58.

It has been discovered that the ratio of the height of the fog nozzle 170 to the height of the cyclonic cup 14 may preferably be in the range of about 0.5 to 1.0. This may have the added advantage of providing more complete filling of the cyclonic cup 14's volume with the desired water fog particles 54, and may also provide some injection of the water fog particles 54 directly into the stripping column 16. If such a ratio is utilized, then it may be preferred that the fog nozzle 170 be tapered, as seen in FIG. 6, since a tapered fog nozzle 170 may limit air flow into the stripping column 16 less, as compared to if the nozzle 170 was not tapered.

It has been further discovered that injecting a fraction of the water fog particles 54 directly into the stripping column 16 may provide full wetting of the inner surfaces of the cyclonic cup 14 and the stripping column 16, with a lower overall water inventory for the air sampler's main body 11 being needed (as compared to if there were no such direct injection of a fraction of the water fog particles 54 directly into the stripping column 16), thereby desirably increasing the concentration of the target material in the water being used.

The desired fraction of the water fog particles 54 that are injected directly into the stripping column 16 for any particular air sampler 10 may be determined by suitable testing of prototype air samplers 10, and may depend on such factors as the viscosity of the stripping liquid; the diameters of the cyclonic cup 14 and the stripping column 16; the rate of the air flow through the cyclonic cup 14 and the stripping column 16; and the velocity of the air rotating within the cyclonic cup 14 and the stripping column 16.

Although the fog nozzle 170 is illustrated as being generally conical in shape, it may have any other suitable shape, such as cylindrical, spherical or inverted conical, for example.

The passive fog generating slot 168 and the spiral nozzle 170 may be optional; but if used, they may be used in addition to, or in place of, the fog generator 34.

In general, whether the water fog particles 54 are produced by the fog generating means 34, 168 and/or 170 (and/or by any other fog generating means), and regardless of whether the target material is in the form of a solid, a liquid or a vapor, the water fog particles 54 may provide extremely high efficiencies for stripping the target material from the incoming air, due to the very large combined surface area of the water fog particles 54, and due to the thorough mixing of the water fog particles 54 and the incoming air within the air inlet tube 32 and the main body 11 of the air sampler 10.

THEORETICAL CONSIDERATIONS REGARDING THE WATER FOG PARTICLES 54:

Regardless of how the water fog particles 54 may be produced, it is conventional knowledge that the mass transfer coefficient per unit area, H, for a spherical water fog particle 54 in an infinite flow stream may obey the following relation, assuming that the target material is in the form of a vapor, by way of example:

$$H = \frac{C_{ta}D_{at}}{D_p}\left[2 + 0.6\sqrt{Re}\,Sc^{1/3}\right] \quad (1)$$

where:

$$Sc = \frac{\mu_a}{\rho_a D_{at}} \quad (2)$$

and $$Re = \frac{\rho_a D_p V_p}{\mu_a} \quad (3)$$

and where $C_{ta}$ is the concentration of the target material vapor in the air; $D_{at}$ is the diffusion coefficient for the target material vapor in the air; $D_p$ is the diameter of the water fog particle 54; Re is the Reynold's number; Sc is the Schmidt number; $\rho_a$ is the density of air; $V_p$ is velocity difference of the water fog particle 54 with respect to the air flow; and $\mu_a$ is the viscosity of air.

The Reynold's number may be relatively low for the water fog particle 54, since it may be small and may have a velocity similar to that of the air flow that surrounds and carries it. Accordingly, any beneficial effect that might otherwise be offered by the velocity-sensitive Reynold's number term in the above Equation 1 may be reduced.

However, in all cases the mass transfer coefficient, H, may be inversely proportional to the diameter, $D_p$, of the water fog particle 54. This may mean that the rate at which the water fog particle 54 strips the target material from the air may be enhanced in the range of about 10 times to about 100 times as compared to the stripping rates associated with macroscopic, fixed, wetted surfaces covered with a thin film of an equal volume of liquid water.

It is conventional knowledge that water fog particles 54 (which may be produced from high pressure fog nozzles, for example), may be used to efficiently strip target material from the air in large structures, such as in the stack exhausts of fossil fuel burning electric power plants, for example.

However, it is a discovery that for any given liquid volume of water, using water fog particles 54 to strip the target material from the air in the relatively tiny volume of the air sampler 10 may be vastly superior to using that same given volume of water as a thin film on a macroscopic fixed, wetted surface of the air sampler 10.

The above approach of stripping target material from the air in the air sampler 10 by the use of water fog particles 54 may also offer other advantages that are not readily apparent.

For example, it has been discovered that if $G_t$ is defined as the ratio of the total target material vapor mass transfer per unit volume of air divided by the total liquid volume of the water fog particles 54 suspended in that air, then $G_t$ will provide a quantitative measure of the mass transfer effectiveness of the water fog particles 54. It may be shown that:

$$G_t = \frac{6C_{ta}D_{at}}{D_p^2}\left[2 + 0.6Re^{0.5}Sc^{1/3}\right] \quad (4)$$

Thus, the above equation 4 shows that, for any given liquid volume of water fog particles 54 in a given volume of air, the mass transfer rate of the target material to the water fog particles 54 may be inversely proportional to the square of the diameter of the water fog particles 54. Accordingly, there may be several advantages to using small water fog particles 54, as compared to using larger water fog particles 54.

A first advantage to using small water fog particles 54 may be that they may strip the target material from the air in much less time, as compared to if larger water fog particles 54 were used. In other words, any desired minimum concentration of the target material in the small water fog particles 54 may be reached in much less time, as compared to if larger water fog particles 54 were used. The importance of this may be appreciated when it is recalled that the target material may be present in the air in only a few parts per billion or in only a few parts per trillion; and that the air sampler 10 may need to strip the target material from large volumes of air before it may reach concentrations in the water fog particles 54 that are detectable by the detection apparatus 67. Thus, the faster the target material is stripped from the air, the faster the detection apparatus 67 will be able to detect the presence, amount and/or identity of the target material. Detection speed may be crucial in certain circumstances, such as where the main body 11 is providing water samples that may contain the target material to a detection apparatus 67 that is seeking to detect target materials such as nerve gas, or the vapors from explosives in luggage or land mines.

For example, 10 micron water fog particles 54 may initially strip the target material from the air 4 times as fast as 20 micron water fog particles 54; meaning that the desired minimum concentration of target material may be reached in the 10 micron water fog particles 54 in about ¼ of the time required by 20 micron water fog particles 54. This may mean that if 10 micron water fog particles 54 were used, then the detection apparatus 67 may be able to detect the presence, amount and/or identity of the target material in about ¼ of the time needed if 20 micron water fog particles 54 were used. A second advantage to using small water fog particles 54 may be that the total amount of water needed by the air sampler 10 may be reduced, as compared to if larger water fog particles 54 were used. For example, a ¼ cc (cubic centimeter) liquid volume of 10 micron water fog particles 54 may initially strip the target material from the air at the same rate at which a 1 cc liquid volume of 20 micron water fog particles would do so.

A third advantage may be that an air sampler 10 using small water fog particles 54 may be more human-portable, since it may consume less power, be smaller, and be lighter, as compared to an air sampler 10 which used larger water fog particles 54. It may consume less power because, as was just explained above, a much smaller liquid volume of small water fog particles 54 may be needed to achieve any particular desired stripping rate. In addition, a smaller volume of air may also need to be moved through the air sampler 10 in order to transport the needed amount of target material through the air sampler 10. Thus, it may take less power to produce that smaller liquid volume of small water fog particles 54, to transport that smaller liquid volume of water through the air sampler 10, and to transport that smaller volume of air through the air sampler 10; as compared the power needed to produce a larger liquid volume of larger water fog particles 54, to transport that larger liquid volume of water through the air sampler 10, and to transport that smaller volume of air through the air sampler 10. Less power consumption may be important because it may mean that any given battery power supply for the air sampler 10 may last longer.

An air sampler 10 using small water fog particles 54 may also be smaller and lighter because, as was just explained above, it may consume less power, and thus it may need smaller or lighter batteries as compared to if it used larger water fog particles 54. In addition, since the total amount of water needed to operate the air sampler 10 may be less if small water fog particles 54 are used, the needed water, as well as its supply container 83, may weigh less and occupy less space.

In this regard, it has been discovered that if it is assumed that the water fog particles 54 are well mixed with the surrounding air, and that mass transfer of the target material vapor to the water fog particles 54 is governed by the above Equation 1, then the time, $\tau_{50}$, required for the water fog particles 54 to extract 50% of the target material vapor from the air may be found to be:

$$\tau_{50} = \frac{0.693D_p^2}{\left[6V_w^*D_{qt}\left(2 + 0.6Re^{0.5}Sc^{1/3}\right)\right]} \quad (5)$$

were $V_w^*$ is the liquid volumetric fraction of water fog particles 54 in a given volume of air.

As a result, it is seen that small water fog particles 54 may be very beneficial since they may significantly reduce mass transfer times. For example, for 10 micron water fog particles 54 $\tau_{50}$ is on the order of about 0.125 seconds for a target material (such as the poison gas phosgene) at 20° C. (centigrade), under stagnant air conditions, where $V_w^*=10^{-5}$. By way of comparison, for 20 micron water fog particles 54 $\tau_{50}$ would be on the order of about 0.5 seconds.

The Cyclonic Cup 14:

As seen in FIGS. 1 and 3–6, the cyclonic cup 14 may comprise a base 56, a cover 62, a sidewall 70, and a generally cylindrical air chamber 76 defined by the base 56, the cover 62 and the sidewall 70.

The base 56 may have an inner surface 58 and a water input port 60. The cover 62 may have an inner surface 64; and an air outlet 68, in which the lower end of the stripping column 16 may be mounted. The sidewall 70 may have an inner surface 72; and an air inlet 74, in which one end of the air inlet tube 32 may be mounted.

In the discussion which follows, it will be assumed that water is being supplied to the cyclonic cup 14 from the water input port 60 (either directly or through a passive fog generating slot 168 or a passive fog generating nozzle 170), and/or from the fog generator 34 in the form of water fog particles 54. However, as was mentioned above, the fog generator 34 may be eliminated, in which case all of the water for the cyclonic cup 14 may be provided from the water input port 60, either directly or through a passive fog generating slot 168 or a passive fog generating nozzle 170. Similarly, if sufficient water is being provided in the form of water fog particles 54 from the fog generator 34, then no water may need to be supplied to the cyclonic cup 14 through its water input port 60 (either directly or through a passive fog generating slot 168 or a passive fog generating nozzle 170).

For better flow of the incoming air into the air chamber 76, the internal diameter of the air inlet tube 32 may be selected to be about equal to the internal radius of the air chamber 76.

Figure 3:
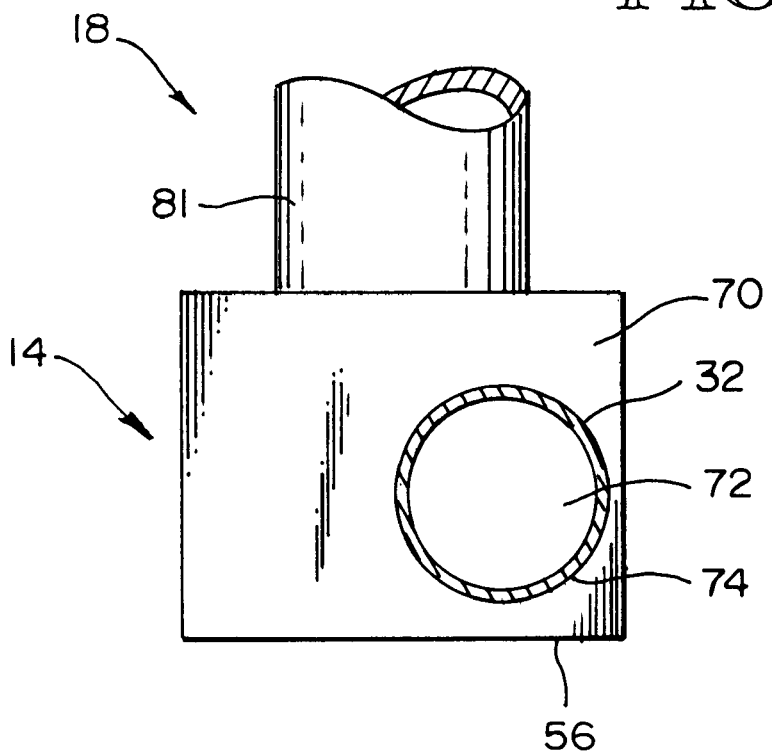
FIG. 3 is a side elevational view, taken along line 3—3 of FIG. 1.
Figure 4:
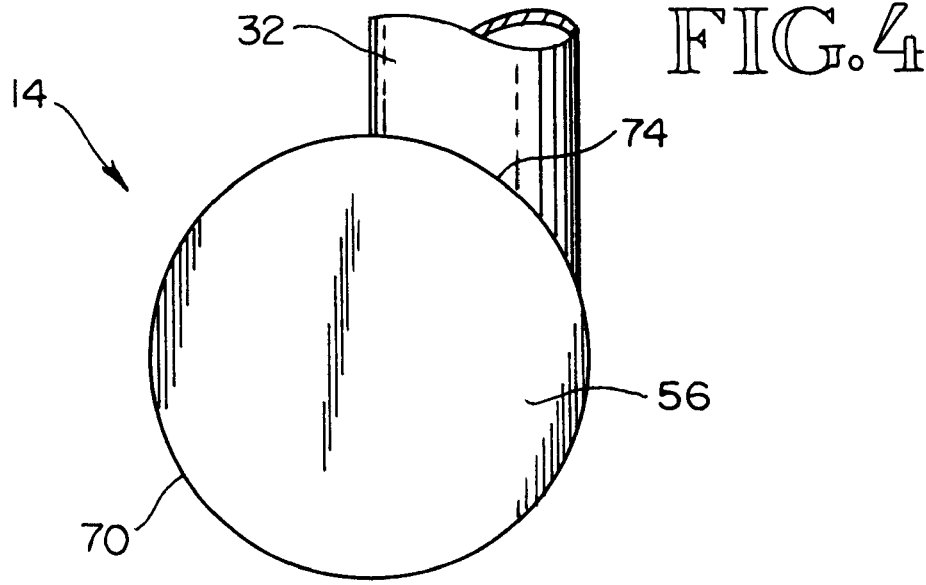
FIG. 4 is a bottom elevational view, taken along line 4—4 of FIG. 1.

As best seen in FIGS. 3–4, the cyclonic cup's air inlet 74 may be located in the sidewall 70 in an offset location, so that the incoming air from the air inlet tube 32 may enter the air chamber 76 tangentially. This may cause the incoming air to swirl within the air chamber 76 and form an air vortex within the air chamber 76 that extends up into the target material stripping column 16 and the demister 18.

Alternatively, any other suitable means may be used to cause the incoming air to swirl within the air chamber 76. For example, the incoming air from the air inlet tube 32 may enter non-tangentially through the sidewall, or may enter through the base 56 or the cover 62, but be directed into the desired swirling motion within the air chamber 76 by one or more suitable vanes located in the air chamber 76.

Advantage may be taken of the centrally located low pressure area in the air chamber 76 that may be created by the air vortex in the air chamber 76. This may be done by locating the water input port 60 in the center of the base 56, and thus in the center of the low pressure area, so that there may be little or no pumping needed in order to move any water into the air chamber 76 through the water input port 60 (and through any passive fog generating slot 168 or nozzle 170 that may be used with the input port 60). In fact, if the pressure in the low pressure area is low enough, it may even make the cyclonic cup 14 self-pumping, since the low pressure area may be sufficient to aspirate water into the air chamber 76 through the water input port 60 (and through any passive fog generating slot 168 or nozzle 170), without any external pumping means needed.

If no passive fog generating slot 168 or passive fog generating nozzle 170 is used with the input port 60, then the air vortex within the air chamber 76 may force the incoming water from the input port 60 to move radially outwardly across the bottom wall 56's inner surface 58 to the sidewall 70's inner surface 72, thereby wetting the inner surface 58 and creating a thin water film on the inner surface 58.

On the other hand, if a fog generating slot 168 or a fog generating nozzle 170 is used with the input port 60, and/or if a fog generator 34 is used, then a thin water film on the inner surface 58 may be created by the coalescence thereon of some of the water fog particles 54 from the slot 168, the fog nozzle 170 and/or the fog generator 34.

In any event, once created, the thin water film on the wetted inner surface 58 may serve the dual functions of helping to strip the target material from the incoming air, and of helping to coalesce into a thin water film the water fog particles 54 (which may carry stripped target material).

Once the thin water film on the base's inner surface 58 reaches the sidewall 70, the shear forces between the water and the upwardly rising air vortex within the air chamber 76 may cause the water to move around, and up, the sidewall 70's inner surface 72 in a generally helical path, thereby wetting the sidewall's inner surface 72 and creating a thin water film on the inner surface 72. If a fog generating slot 168 or nozzle 170 is used with the input port 60, and/or if a fog generator 34 is used, then the inner surface 72 may also be wet by the coalescence thereon by of some of the water fog particles 54 from the slot 168, the fog nozzle 170 and/or the fog generator 34.

In any event, once created, the thin water film on the wetted inner surface 72 may serve the dual functions of helping to strip the target material from the incoming air, and of helping to coalesce into a thin water film the water fog particles 54 (which may carry stripped target material).

Although the inner surface 72 of the cyclonic cup 14's sidewall 70 is illustrated in FIG. 1 as being straight, and as intersecting the base 56 at a right angle, the inner surface 72 may be concave, and form a smoothly curved intersection with the base's inner surface 58, for better flow of the air within the air chamber 76, and for better flow of the water from the base's inner surface 58 to the sidewall's inner surface 72. Alternatively, the sidewall's concave inner surface 72 may extend all the way to the input port 60, so that the base 56 may have no separate inner surface 58. In any event, the concave shape of the sidewall's inner surface 72 may be selected such that during operation of the air sampler 10 the water film formed on the inner surface 72 may be of at least substantially uniform thickness. A water film having at least substantially uniform thickness may be desirable because then there may be no dry spots on the surface 72 that may be unable to strip target material from the air or to coalesce water fog particles 54, and because then there may be no water traps in the inner surface 72 that might otherwise slow down or interrupt the passage of the water across the inner surface 72.

It has been discovered that the wettability of the cyclonic cup's inner surfaces 58, 72 may be very important. This is because if the inner surfaces 58, 72 are wettable, i.e., are hydrophilic, complete surface coverage of the inner surfaces 58, 72 with a water film may be achieved with much thinner water films, as compared to if the inner surfaces 58, 72 were not wettable, i.e., were hydrophobic. Such thinner water films may be very important since they may reduce the amount of water needed to strip the target material from the air vortex within the air chamber 76; thereby desirably increasing the concentration of the stripped target material in the water film. In addition, the presence of a thin water film on the inner surfaces 58, 72 may enhance their ability to coalesce the water fog particles 54 into a thin water film.

The water itself may be treated with any known surfactant to improve its wettability, as long as the surfactant is compatible with the detection apparatus 67, **67*a*; and as long as the surfactant possesses either, or both, of the following properties: (a) the surfactant may be "non-foaming", i.e., it must not generate an amount of foam that would interfere with the proper operation of the air sampler 10**; and (b) the surfactant may increase the solubilization of the target material, if the target material comprises insoluble or moderately insoluble molecules (such as the explosive TNT).

Suitable surfactants may be Surfynol 465 (comprising 2,4,7,9-tetramethyl-5-decyne-4,7-diol ethoxylate (10)) or Surfynol 485 (comprising 2,4,7,9-tetramethyl-5-decyne-4,7-diolethoxylate (30)), both manufactured by the Air Products and Chemicals Company; Aerosol OT (comprising sodium dioctylsulfosuccinate), manufactured by the American Cyanamide Co.; and Surfactant 10G (comprising p-(nonylphenoxy)poly(glycidol)), manufactured by the Olin Corporation.

Alternatively, the water may be treated with a binding material that binds the target material and increases the effective partition coefficient of the target material, thereby increasing the concentration of the target material in the water. This alternative may be particularly effective for target materials having very low water solubilities, such as the pesticide, DDT; or having adequate water solubility but a relatively high vapor pressure, such as, for example, a low molecular weight alcohol such as methanol. For example, such a binding material might comprise an antibody dissolved in the water that is selective for the target material. The negligible vapor pressure of the antibody may effectively prevent its removal from the water through evaporative processes. The concentration of the target material in the water would increase as the target material partitioned between the air and water phases within the air sampler's main body 11, and was bound by the antibody during operation of the air sampler 10.

As a further alternative, the binding material may be formed by polymerizing hydroxyethyl methacrylates in the presence of the target material. During polymerization, or after polymerization is complete, the resulting polymer can be processed or sorted into about 1–20 micron polymer binding material particles and washed to remove the target material as well as residues of the reaction process. If exposed to a solution of the target material, such a binding material will bind, to a greater or lesser extent, some of the target material. Again, this technique provides a method of increasing the effective partition coefficient of a target material in water as compared to if such a binding material were not used.

As an additional alternative, it is now possible to design proteins to serve a desired function by examining the structures of proteins of known functions. Thus, it may be possible to design a binding material protein that is able to bind with the target material and increase the effective partition coefficient of the target material, such as where the target material comprises any of the triazine class of pesticides. Such a binding material protein may be added to the water in the air sampler 10, where it would enhance the partition coefficient for the target material, thereby increasing the concentration of the target material in the water.

All of the above comments regarding surfactants, and regarding binding materials for increasing the effective partition coefficient for the target material, may apply equally well to the water used in the air sampler 130 of FIG. 9 and the air sampler 200 of FIG. 12.

In any event, as was explained previously, as used herein the terms “wetted”, “wetted”, “wettable”, “wettability”, “hydrophilic”, “hydrophobic”, and the like, are to be interpreted as having meanings with respect to non-aqueous stripping liquids that correspond to their meanings when used with aqueous stripping liquids.

Making the cyclonic cup's inner surfaces 58, 72 wettable or hydrophilic may be done in several ways. For example, the cyclonic cup 14 may be made from a hydrophilic material, such as ceramic, glass or oxide coated metal; or its inner surfaces 58, 72 may be coated with a layer of a hydrophilic material.

Alternatively, it has been discovered that another way of making the cyclonic cup 14's inner surfaces 58, 72 wettable or hydrophilic may be to make the cyclonic cup 14 from a plastic material, and to then chemically alter its inner surfaces 58, 72 in such a way so as to make them wettable or hydrophilic.

Two suitable plastic materials from which such a cyclonic cup 14 may be made may comprise cellulose acetate and cellulose acetate butyrate. A cyclonic cup 14 made from such materials may then be immersed in a potassium hydroxide solution having a concentration of about 20% w/v (weight per unit volume), at 60° C., for a period of 8–24 hours, to produce a continuously graded cellulosic junction with the completely unreacted substrate plastic material. The continuously graded cellulosic junction may comprise an effectively pure cellulosic layer at, and beneath, the inner surfaces 58, 72. The effectively pure cellulosic layer may be about one micron thick, for example. Since the chemical reaction occurs at the unreacted substrate/cellulosic interface, the thickness of the continuously graded cellulosic junction, and the thickness of its effectively pure cellulosic layer, may vary approximately as the square root of time, in agreement with a typical diffusion-dominated reaction, for any given concentration of potassium hydroxide and for any given temperature. A continuously graded cellulosic junction, and/or its effectively pure cellulosic layer, having any particular desired respective thickness may be achieved in less time by increasing the concentration of the potassium hydroxide solution and/or by increasing the reaction temperature, within reason.

It has been also been discovered that the continuously graded junction that is produced by above method may offer the important advantage of being resistant to harm. This may be due to the continuously graded junction having a relatively substantial thickness, as compared to a monolayer-thick coating of hydrophilic material that may be easily damaged; and may also be due to the continuously graded junction being an integral part of the plastic material, which may make it relatively immune to the peeling or delamination that might otherwise occur if the inner surfaces 58, 72 were simply coated with a cellulosic film or coating.

The treatment of cellulose acetate or cellulose acetate butyrate with sodium hydroxide that was described above is an example of a chemical reaction involving hydrolysis. Other hydrolysis reactions that may be used to produce wettable or hydrophilic inner surfaces 58, 72 may involve making the cyclonic cup 14 from condensation polymers such as polyesters, polyamides, and polycarbonates. The inner surfaces 58, 72 of such a cyclonic cup 14 may then be chemically altered by treating it with suitable basic hydrolytic reagents, such as sodium or potassium hydroxide, or acidic hydrolytic reagents, such as sulfuric acid or hydrochloric acid. Suitable reaction temperatures may be in the range of about 25° C. to 60° C., and suitable reaction times may be about 1 to 24 hours.

Two alternative chemical approaches for making the cyclonic cup 14's inner surfaces 58, 72 wettable or hydrophilic may involve two other general types of reactions, other than hydrolysis reactions. These alterative chemical approaches may also produce a graded junction between the altered inner surfaces 58, 72 that were made wettable or hydrophilic, and the completely unreacted portion of the substrate material.

The first such alternative chemical approach may involve oxidation reactions. For example, the cyclonic cup 14 may be made from polyolefin materials such as polypropylene, or olefin containing copolymers such as ABS (acrylonitrile-butadiene styrene). The cyclonic cup 14's inner surfaces 58, 72 may then be chemically altered by immersing the cyclonic cup 14 in chromic acid or potassium permanganate.

In oxidation reactions, carbon-carbon bonds in the cyclonic cup 14 may be broken, and hydroxylated surfaces may be produced that are wettable or hydrophilic. The oxidation reactions may occur at about room temperature in reasonable periods of time, i.e., in the range of about 1–24 hours.

The second such alternative chemical approach may involve reduction reactions. For example, the cyclonic cup 14 may be made from highly halogenated polymers, such as polytetrafluoroethylene (Teflon) or polyvinylidine fluoride. The reagent may be sodium naphthalide in any suitable etherial solvent, such as diglyme. The reactions may occur in the range of about 10° C. to 30° C. and may take in the range of about 1 to 24 hours. In reduction reactions, the carbon-halogen bonds are cleaved homolytically and then may react with oxygen and water to form hydroxylated hydrophilic surfaces 58, 72.

A further alternative approach for making the cyclonic cup 14's inner surfaces 58, 72 wettable or hydrophilic may be to make the cyclonic cup 14 from a suitable metal, and to then anodize its inner surfaces 58, 72. For example, suitable metals may be aluminum, copper or stainless steel; and suitable anodizing chemicals may be any standard commercial anodizing process for producing an impervious oxide coat.

Another alternative approach for making the cyclonic cup 14's inner surfaces 58, 72 wettable or hydrophilic may be to make the cyclonic cup from a material that is etchable by an etchant, and to then etch the inner surfaces 58, 72 with an etchant, in order to slightly roughen the inner surfaces 58, 72. For example, a suitable etchable material may be glass; and suitable etchants may be hydrofluoric acid, or buffered hydrofluoric acid. The etching reactions may occur in the range of about 5.0° C. to 50° C.; and may take from a few minutes to a few hours, depending on the glass type.

An additional alternative approach for making the cyclonic cup 14's inner surfaces 58, 72 wettable or hydrophilic may be to etch the inner surfaces 58, 72 with a radio-frequency plasma. In general, such plasma-etching may be used with a cyclonic cup 14 made from nearly any type of plastic, and may involve using a radio-frequency discharge to ionize a reaction gas, such as argon, oxygen or ammonia. The positive ions in the reaction gas may react with the inner surfaces 58, 72, abstracting hydrogen atoms from the plastic's carbon-hydrogen bonds to form radicals on the inner surfaces 58, 72. After the plasma exposure is stopped, the desired hydroxylated surfaces that are wettable and hydrophilic may be created by reacting the radicals formed on the inner surfaces 58, 72 with air and water vapor, or with reactive compounds such as hydroxyethyl methacrylate or acrylic acid, that are hydrophilic and stable once bonded to the inner surfaces 58, 72.

A further alternative approach for making the cyclonic cup 14's inner surfaces 58, 72 wettable or hydrophilic may be to slightly roughen the inner surfaces 58, 72, such as by sandpapering them or sandblasting them.

Returning now to the construction and operation of the cyclonic cup 14, once the water film reaches the top of its sidewall's inner surface 72, the shear forces between the water and the upwardly rising air vortex within the air chamber 76 may cause the water film to move radially inwardly across the inner surface 64 of the cover 62 of the cyclonic cup 14, thereby wetting the inner surface 64 and creating a thin water film on the inner surface 72. If a fog generating slot 168 or nozzle 170 is used with the input port 60, and/or if a fog generator 34 is used, then the inner surface 64 may also be wet by the coalescence thereon by of some of the water fog particles 54 from the slot 168, the fog nozzle 170 and/or the fog generator 34.

In any event, once created, the thin water film on the wetted inner surface 64 may serve the dual functions of helping to strip the target material from the incoming air, and of helping to coalesce into a thin water film the water fog particles 54 (which may carry stripped target material).

Although the inner surface 72 of the cyclonic cup 14's sidewall 70 and the inner surface 64 of the cover 62 are illustrated in FIG. 1 as being straight, and as intersecting with each other at a right angle, the inner surfaces 64, 72 may be concave, and form a smoothly curved intersection with each other, for better flow of the air within the air chamber 76, and for better flow of the water from the sidewall's inner surface 72 to the cover's inner surface 64. The concave shape of the inner surfaces 64, 72 may be selected such that during operation of the air sampler 10 the water film formed on the inner surfaces 64, 72 may be of at least substantially uniform thickness. A water film having at least substantially uniform thickness may be desirable because then there may be no dry spots on the inner surfaces 64, 72 that may be unable to strip target material from the air or to coalesce water fog particles 54, and because then there may be no water traps in the inner surfaces 64, 72 that might otherwise slow down or interrupt the passage of the water across the inner surfaces 64, 72.

The arrow 78 in FIG. 1 illustrates the general path that may be followed by the thin water film in the cyclonic cup 14 from its water input port 60 to the cover's outlet 68.

As an alternative, the cyclonic cup 14's entire cover 62 may be eliminated. In such an event, the external diameter of the stripping column 16 may selected to be about equal to the internal diameter of the cyclonic cup 14 (for a snug, air-tight fit therebetween), so that the stripping column 16's bottom edge 162 may serve the function of the inner surface 64 of the cover 62. With such a construction, the water film driven up the cyclonic cup's inner surface 72 by the air vortex within the cyclonic cup 14 may flow directly onto the stripping column 16's bottom edge 162 and inner surface 82. As was the case with the cover's inner surface 64, the bottom edge 162 of the stripping column 16 may be concave, and form a smoothly curved intersection with the inner surface 72 of the cyclonic cup 14.

It has been discovered that the wettability of the inner surface 64 of the cyclonic cup's cover 62 may be very important for the reasons set forth above regarding the wettability of the cyclonic cup 14's inner surfaces 58, 72; and may be achieved in a manner like that described above regarding the inner surfaces 58, 72.

As was described above, the low pressure area created by the air vortex within by the cyclonic cup 14 may serve to help make the air sampler self-pumping, in that no external pumps may be needed to force the water into the cyclonic cup 14 from its water input port 60. However the air vortex within the cyclonic cup 14, which may extend upwardly into the stripping column 16 and the demister 18, may also serve to help make the air sampler self-pumping in another manner, since the air vortex itself may transport the water from the cyclonic cup 14's input port 60 in a thin water film across the inner surfaces of the cyclonic cup 14, the cover 62, and the stripping column 16; and into the demister 18.

Thus, it may be preferred that the velocity of the incoming air from the air inlet tube 32, and the internal sizes and shapes of the cyclonic cup 14 and the stripping column 16 be selected to enable the air vortex created by the incoming air to "pump" the water film through the cyclonic cup 14 and the stripping column 16, and into the demister 18, in the manner described above.

From all of the forgoing, it is seen that the cyclonic cup 14 may serve many important functions. Those important functions may include: (a) creating from the incoming air a rapidly spinning air vortex within the air chamber 76 that extends upwardly into the stripping column 16 and the demister 18; (b) using the air vortex in its air chamber 76 to permit, or assist, the entry of water through its water input port 60; (c) using the air vortex in its air chamber 76 to create a thin water film on the inner surfaces 58, 64 and 72; (d) using the interaction between the air vortex in its air chamber 76 and the water film on the inner surfaces 58, 64 and 72 to assist the thin water film in serving the dual functions of helping to strip target material from the incoming air and of helping to coalesce into a thin film of water the water fog particles 54 produced by the slot 168, the nozzle 170 and/or the fog generator 34; and (d) using the air vortex in its air chamber 76 to pump the water on the inner surfaces 58, 64, and 72 up and onto the inner surface 82 of the stripping column 16.

The Target Material Stripping Column 16:

As seen in FIG. 1, the target material stripping column 16 may comprise a sidewall 81; and a generally cylindrical air chamber 84 defined by the sidewall 81. The sidewall 81 may have an inner surface 82, a top edge 65 and a bottom edge 162.

Although the air chamber 84 is illustrated as having a generally cylindrical shape, it may have any other suitable shape, such as conical. If it has a conical shape, it may be preferred that the narrow end of the cone be at the bottom of the stripping column 16. Although the sidewall 81 and its inner surface 82 are illustrated as being relatively straight in a vertical direction, they may be curved inwardly and/or outwardly one or more times along their vertical length.

The diameter of the stripping column 16's air chamber 84 may be smaller than the diameter of the cyclonic cup's air chamber 76. As a result, the air vortex within the air chamber 84 may rotate at a higher speed than the air vortex within the air chamber 76. Such higher speed rotation of the air vortex within the air chamber 84 may have at least two beneficial effects.

The first beneficial effect of such higher speed rotation of the air vortex within the air chamber 84 may be that it may cause the pressure within the air chamber 84 to be less than that in the air chamber 76, due to the Bernoulli effect, thereby permitting the relatively higher pressure in the air chamber 76 to help "pump" the thin film of water from the inner surface 64 of the cyclonic cup's cover 62 onto the inner surface 82 of the stripping column 16.

Once the thin film of water from the inner surface 64 of the cyclonic cup's cover 62 reaches the stripping column's inner surface 82, the shear forces between the thin film of water and the upwardly rising air vortex within the air chamber 84 may cause the thin film of water to move around, and up, the inner surface 82 in a generally helical path, thereby wetting the inner surface 82 and creating a thin water film on the inner surface 82.

On the other hand, if a fog generating slot 168 or nozzle 170 is used with the input port 60, and/or if a fog generator 34 is used, then the thin water film on the inner surface 82 may also be created by the coalescence thereon of at least some of the water fog particles 54 from the slot 168, the nozzle 170, and/or the fog generator 34.

In any event, once created, the thin water film on the wetted inner surface 82 may serve the dual functions of helping to strip the target material from the incoming air, and of helping to coalesce into a thin water film the fog particles 54 (which may carry stripped target material).

Once the thin water film reaches the top of the stripping column's inner surface 82, it may then be forced by the air vortex within the demister 18 to move radially outwardly across the top edge 65 of the stripping column 16, until gravity pulls it down into the demister's reservoir 53. secondary air circulation patterns in the demister 18 may also result in downward air flow ear the inner surface 49 of the demister's sidewall 49, providing an additional downward force on any suspended water fog particles 54.

The second beneficial effect of the higher speed rotation of the air vortex within the stripping column 16's air chamber 84 is that it may enable the stripping column's wetted inner surface 82 to more efficiently strip particle-type target material from the incoming air, and to more efficiently coalesce into a thin water film the water fog particles 54 (which may carry stripped target material). This is because the higher speed of rotation of the air vortex within the air chamber 84 may generate corresponding greater centrifugal forces, and greater turbulence at the air/water film interface, that may more effectively drive particle-type target 12 material and the water fog particles 54 onto the stripping column's wetted inner surface 82.

On the other hand, if the target material is in the form of a vapor, then the higher speed of rotation of the air vortex within the air chamber 84 may increase the ability of the thin water film on the stripping column's wetted inner surface 82 to strip the target material vapor from the air, due to the more turbulent interaction that may occur at the water film/air vortex interface.

As seen in FIG. 1, the stripping column's inner surface 82 may be provided with shallow spiral grooves 88 and bosses 90, like a screw's threads, that may be cut or molded into the inner surface 82. The sides of the grooves 88 may have sharply angular intersections with the bottoms of the grooves 88 and the tops of the bosses 90, as is also seen in FIG. 1. Alternatively, the sides of the grooves 88 may have smoothly contoured intersections with the bottoms of the grooves 88 and/or with the tops of the bosses 90. For example, the cross-sectional configuration of the grooves 88 and bosses 90 may have a sinusoidal-like shape.

In order to encourage the water film from the inner surface 64 of the cyclonic cup's cover 62 to follow the spiral path provided by the grooves 88 and bosses 90 on the inner surface 82 of the stripping column 16, it may be preferred that the grooves 88 and bosses 90 spiral upwardly in the same direction that the rising air vortex spins within the air chamber 84. For example, for the grooves 88 and bosses 90 that are illustrated in FIG. 1, the rising air vortex within the air chamber 84 may be spinning clockwise (as viewed from the bottom of the stripping column 16).

The depth, shape, length and/or pitch of the grooves 88 may be selected to permit the grooves 88 to perform a variety of functions. A first function of the grooves 88 may be that they may provide shelter for the thin water film that they may carry on the inner surface 82 of the stripping column 16, in order to avoid as much as possible undesirable entrainment of that water film by the air vortex within the stripping column's air chamber 84.

A second function of the grooves 88 may be that, despite any sheltering function, they may also permit good contact between the water film they carry and the air vortex, to permit the water film to strip the target material from the air and to coalesce the water fog particles 54 into a thin water film at the maximum possible efficiency.

In order to perform this second function most effectively, it may be preferred: (a) that the pitch of the grooves 88 approximate the natural pitch of the rising air vortex within the stripping column 16 (i.e., the pitch the rising air vortex would have if the stripping column's inner surface 82 was smooth and had no grooves 88 or bosses 90); (b) that the total surface area of grooves' bosses 90 account for about 20%, or less, of the total surface area of the stripping column's inner surface 82; and/or (c) that the total surface area of the grooves 88 account for about 80%, or more, of the total surface area of the stripping column's inner surface 82.

To some extent, the air vortex within the stripping column 16 may be made to spin with a tighter pitch than might otherwise be the case by increasing the number of grooves 88 and bosses 90 per unit length of the stripping tube 16 (i.e., by decreasing the pitch of the grooves 88 and bosses 90), and vice versa. Making the air vortex within the stripping column 16 spin with a tighter pitch may desirably increase the collection of the target material by the thin film of water on the stripping column's inner surface 82: (a) by increasing the residence time within the stripping column 16 of the air (and the residence time of any target material and water fog particles 54 carried by the air); and (b) by maximizing the contact between the thin film of water on the stripping column's inner surface 82 and the air (and any target material and water fog particles 54 carried by the air).

A third function of the grooves 88 may be that, despite any sheltering function, they may also allow some of the water film they carry to "leak" onto the bosses 90 between adjacent grooves 88, as a result of air/water shear between the air vortex and the water film. Such leakage of some of the water film from the grooves 88 may be desirable since it may permit the stripping column's entire inner surface 82 to be wet with a thin water film, thereby increasing the ability of the inner surface 82 to strip the target material from the air and to coalesce the water fog particles 54 into a thin water film.

A fourth function of the grooves 88, and their bosses 90, may be to dramatically increase the efficiency with which the stripping column's wetted inner surface 82 may strip the target material from the air and coalesce the water fog particles 54 into a thin water film, by increasing the surface area of the wetted inner surface 82 (as compared to if there were no grooves 88 and bosses 90). In general, the greater the surface area of the wetted inner surface 82, the greater the ability of the thin water film on the wetted inner surface 82 to strip the target material from the air and to coalesce the water fog particles 54 into a thin water film. However, such increasing of the surface area of the wetted inner surface 82 may increase the overall drag of the inner surface 82 on the air passing through the stripping column 16, and may increase the air pressure drop across the stripping column 16.

A fifth function of the grooves 88 and bosses 90 may be to dramatically increase the efficiency with which the stripping column's wetted inner surface 82 may strip the target material from the air and coalesce the water fog particles 54 into a thin water film, by increasing the amount of time that each part of the water film on the inner surface 82 is in contact with the air vortex within the air chamber 84. This is because the grooves 88 and bosses 90 may encourage most, if not all, of the water film from the inner surface 64 of the cyclonic cup's cover 62 to travel in a long spiral path that is at least substantially the same as the spiral path followed by the grooves 88 and bosses 90. Without the grooves 88 and bosses 90, the rapidly rising air vortex within the air chamber 84 may tend to force the water film to follow a much shorter spiral path up the stripping column's inner surface 82 before the water film enters the demister 18.

As an alternative to the grooves 88 and bosses 90, any other suitable flow channel means may be used for adjusting and directing the flow of the water film on the stripping column's inner surface 82 in a manner that is at least generally similar to that provided by the grooves 88 and bosses 90.

As a further alternative, the grooves 88 and bosses 90 may be eliminated from the stripping column's inner surface 82.

It has been discovered that the wettability of the stripping column 16's inner surface 82 (including the surfaces of its grooves 88 and/or bosses 90, if any) may be very important for the reasons set forth above regarding the wettability of the cyclonic cup 14's inner surfaces 58, 72; and may be achieved in a manner like that described above regarding the inner surfaces 58, 72.

The Demister 18:

Once the air vortex has left the stripping column 16, it may then enter the demister 18. The demister 18 may comprise a base 41; a sidewall 47; an air outlet 51; and a reservoir 53 formed between the base 41, the sidewall 47, and the portion of the stripping column 16 that extends into the demister 18.

The base 41 may comprise a water outlet port 43 for the reservoir 53, and a mounting hole 45 for the stripping column 16. The sidewall 47 may comprise an inner surface 49 and define a generally cylindrical air chamber 164. The air outlet 51 may serve as a mounting hole for the fan 20's air inlet 24.

The reservoir 53 may be equipped with a liquid level control means 55 comprising a float 57; a float rod 59; a lower light source/photodiode pair 61; and an upper light source/photodiode pair 63. The float 57 may be slidingly mounted on the float rod 59; the float rod 59 may be secured to the demister's base 41; and the light source/photodiode pairs 61, 63 may be mounted to the demister's sidewall 47, and may have any suitable electrical power and water level signal wiring connections.

As was described in detail earlier, the upwardly rising air vortex within the stripping column 16 may force the water film from the inner surface 64 of the cyclonic cup 14's cover to travel in an upwardly rising, spiral path on the stripping column's wetted inner surface 82. Along the way, the water film may have stripped at least some of the target material from the air vortex, and may have coalesced at least some of the water fog particles 54 (which may also carry stripped target material) into a thin water film on the inner surface 82. Once the water film reaches the top of the stripping column 16, it may be urged radially outwardly across the stripping column's top edge 65 by the air vortex (which extends from the stripping column 16 into the demister's air chamber 164), until the thin film of water (and any target material it carries) spills over into the reservoir 53 under the influence of gravity.

When the rapidly spinning air vortex in the stripping column 16 enters the demister 18, its rotation speed and its vertical speed decline substantially, because the diameter of the demister's air chamber 164 may be substantially larger than the diameter of the stripping column's air chamber 84. As a result, any of the water film on the stripping column's inner surface 82 that may have been entrained by the air vortex within the stripping column 16 may no longer be supported by the less rapidly spinning, less rapidly rising air vortex within the demister's air chamber 164. Accordingly, any formerly entrained water may either fall directly into the reservoir 53; or it may be deposited on the demister's inner surface 49, where it may then run down, under the force of gravity, into the reservoir 53.

Thus, it may be appreciated that the larger diameter of the demister's air chamber 164, as compared to the smaller diameter of the stripping column's air chamber 84 may serve the important dual purposes of creating the reservoir 53, while at the same time reducing the rotation speed and the vertical speed of the air vortex in the air chamber 164, so that the air may drop any entrained water that it may be carrying.

Besides collecting any formerly entrained water, the demister 18 may also serve other important functions. For example, its wetted inner surface 49 may also serve to help strip any remaining target material from the air vortex within the demister's air chamber 164, and may help to coalesce any remaining water fog particles 54 into a thin water film.

Finally, the air may be removed from the demister 18 by the fan 20, which may suck the air into its inlet 24, and expel it from its outlet 26.

It has been discovered that the wettability of the demister 18's inner surface 49 may be very important. This is because if the inner surface 49 is wettable, i.e., is hydrophilic, rather than hydrophobic, there may tend to be less hold-up of the water on the inner surface 49 due to water droplet formation and attachment on the inner surface 49. Thus, if the inner surface 49 is hydrophilic, rather than hydrophobic, any water droplets from the air vortex striking the inner surface 49 will quickly form a water film, or integrate with an existing water film, and run down into the reservoir 53, thereby: (a) improving the response rates of the air sampler 10, (b) reducing the water inventory needed by the air sampler 10, (c) increasing the effectiveness of any washdown and surface cleaning of the inner surface 49, and (d) providing fewer spurious responses by the air sampler 10, which might otherwise result from the sudden release of water droplets from the inner surface 49, such as might be caused by vibration or mechanical jarring of the air sampler 10.

The wettability of the inner surface 49 of the demister 18 may be achieved in a manner like that described above regarding the inner surfaces 58, 72 of the cyclonic cup 14.

THE FLUIDIC CIRCUITRY 22:

The fluidic circuitry 22 may comprise an output conduit 69 for the demister's reservoir 53; a cyclonic cup input valve 71; a cyclonic cup input conduit 166; a fog generator input valve 73; and a fog generator input conduit 158.

The output conduit 69 may convey the reservoir 53's water (which may carry stripped target material) to the cyclonic cup's input port 60 through the cyclonic cup's input conduit 166 when the cyclonic cup's input valve 71 is open. The amount of water passing into the input port 60 may also be regulated by the valve 71.

The output conduit 69 may also convey water from the reservoir 53 to the fog generator 34 through the fog generator's input conduit 158 when the input valve 73 is open. The amount of water passing into the fog generator 34 may also be regulated by the valve 73.

If the cyclonic cup 14 is to be supplied with water from the reservoir 53 by only the fog generator 34, then the valve 71 to the cyclonic cup's input port 60 may be closed; or the valve 71, the conduit 166, and the input port 60 may be eliminated. On the other hand, if the cyclonic cup 14 is to be supplied with water from the reservoir 53 by only its input port 60, then the fog generator valve 73 may be closed; or the fog generator 34 and its the valve 73 and conduit 158 may be eliminated.

Alternatively, if the cyclonic cup 14 is to be supplied with water from the reservoir 53 by both its input port 60 and the fog generator 34, then the proportion of water from the reservoir 53 that is supplied to the cyclonic cup 14 by its input port 60, as compared to that supplied by the fog generator 34, may be selected by making suitable adjustments to the valves 71, 73.

The fluidic circuitry 22 may further comprise a sample conduit 94; a sample pump 75; and a detection apparatus 67 for detecting the presence, amount and/or identity of the target material. Samples from the reservoir 53 may be conveyed to the detection apparatus 67 through the output conduit 69 and the sample conduit 94 when the sample pump 75 is operated. The sample pump 75 may also regulate the rate at which any particular sample from the reservoir 53 is delivered to the detection apparatus 67.

The fluidic circuitry 22 may also comprise a waste conduit 77; a waste pump 79; and a waste container 98. Waste from the reservoir 53 may be conveyed to the waste container 98 through the output conduit 69 and the waste conduit 77, when the waste pump 79 is operated. The waste pump 79 may also regulate the rate at which the waste is delivered to the waste container 98.

Gravity may assist the flow of water from the reservoir 53 to the cyclonic cup's input port 60, the fog generator 34, the detection apparatus 67, and/or the waste container 98, by locating the reservoir 53 higher than the component(s) being gravity fed.

Thus, the cyclonic cup's input port 60 may be fed with water from the reservoir 53 by gravity acting in combination with the low pressure area created by the air vortex within the cyclonic cup 14 around the input port 60. The gravity fed water from the reservoir 53 may be successfully used to supply the fog generator 34 despite its relatively low pressure because, as was described in detail earlier, the fog generator 34 does not rely on high water pressures or restricted nozzles in order to generate the water fog particles 54.

Such gravity assisted feeding of water from the reservoir 53 to the cyclonic cup 14's input port 60 and the fog generator 34 may offer the important advantages of consuming zero electrical energy; and of increasing the reliability, while reducing the cost, weight and complexity of the air sampler 10, due to the elimination of the need to use any pumps and their related valves and conduits. These important advantages may be particularly significant in the context of a human-portable air sampler 10, since lower weight is always important for human-portable devices; and since needing zero energy for pumping the water from the reservoir 53 translates into lower battery weight, or into longer life for a battery of any given weight.

However, as an alternative, a pump may be provided in any suitable location in the fluidic circuitry 22, such as in the output conduit 69 near the reservoir 53, for pumping the water from the reservoir 53 into the air vortex's input port 60, the fog generator 54, the detection apparatus 67, and/or the waste container 98.

The fluidic circuitry 22 may further comprise a fresh water supply container 83; a fresh water supply valve 85; a cleaning solution supply container 87; a cleaning solution supply valve 89; an input conduit 91; a check valve 92; an air pump 93; a compressed air conduit 95; an air check valve 97 for the fresh water supply container 83; and air check valve 99 for the cleaning solution supply container 87. The air pump 93 may be any suitable conventional air pump.

Any suitable cleaning solution may be used, such as a bleach solution comprising about 5% sodium hypochlorite. The particular cleaning solution selected may depend on various factors, such as the nature of the particular liquid(s) being used in the air sampler 10 and the particular target material(s) being detected, for example.

Compressed air from the air pump 93 may be furnished to the fresh water supply container 83 through the compressed air conduit 95 and the air check valve 97; and may be furnished to the cleaning solution supply container 87 through the compressed air conduit 95 and the air check valve 99. The air pump 93 may be provided with an air pressure sensing means for turning the air pump 93 off when the air pressure in the supply containers 83, 87 reaches a predetermined high limit; and for turning the air pump 93 back on when the air pressure in the supply containers 83, 87 reaches a predetermined low limit.

The compressed air in the fresh water supply container 83 may force fresh water out of the container 83 and into the input conduit 91 when the fresh water supply valve 85 is open; while the compressed air in the cleaning solution supply container 87 may force cleaning solution out of the container 87 when the cleaning solution supply valve 89 is open. Fresh water and/or cleaning solution from the input conduit 91 may be supplied to the cyclonic cup 14 through the output conduit 69, the valve 71 and the conduit 166; and may be supplied to the fog generator 34 through the output conduit 69, the valve 73 and the conduit 158. The amount of fresh water and/or cleaning solution that are supplied to the cyclonic cup 14 and the fog generator 34 from the input conduit 91 may be controlled by the air pressure within the containers 83, 87, and/or by how much the valves 85, 89, 71, 73 are opened.

If the cyclonic cup 14 is to be supplied with fresh water and/or cleaning solution from the containers 83, 87 by only the fog generator 34, then the valve 71 to the cyclonic cup's input port 60 may be closed; or the valve 71, the conduit 166, and the input port 60 may be eliminated. On the other hand, if the cyclonic cup 14 is to be supplied with fresh water and/or cleaning solution from the containers 83, 87 by only its input port 60, then the fog generator valve 73 may be closed; or the fog generator 34 and its the valve 73 and conduit 158 may be eliminated.

Alternatively, if the cyclonic cup 14 is to be supplied with fresh water and/or cleaning solution from the containers 83, 87 by both its input port 60 and the fog generator 34, then the proportion of fresh water and/or cleaning solution that is supplied to the cyclonic cup 14 by its input port 60 as compared to that supplied by the fog generator 34 may be selected by making suitable adjustments to the valves 71, 73.

When liquid is flowing through the input conduit 91 from either of the containers 83, 87, the check valve 92 may prevent back flow of the liquid into the output conduit 69 towards the detection apparatus 67. Alternatively, the check valve 92 may be eliminated if the pressure and/or flow rates of liquid in the input conduit 91 are low enough with respect to the pressure and/or flow rates of liquid in the output conduit 69, so that such back flow does not occur during operation of the air sampler 10.

Alternatively, instead of using compressed air, any suitable liquid pump may be used to force the liquids out of the supply containers 83, 87 and into the input conduit 91; and may be located in any suitable place in the fluidic circuitry 22, such as in the input conduit 91. However, using compressed air may be preferred over using a liquid pump, since an air pump 93 may have a longer life and be more energy efficient than a liquid pump. This may be due to the fact that the air pump 93 is on only when it is in the process of pressurizing the containers 83, 87; is off at all other times; and is not subjected to wet and potentially corrosive or fouling liquids.

Alternatively, the liquids from the supply containers 83, 87 may be gravity fed to the cyclonic cup's input port 60 and to the fog generator 34, by locating the supply containers 83, 87 higher than the cyclonic cup 14's input port 60 and higher than the fog generator's tip 160. In such an event, the air pump 93, the compressed air conduit 95, and the check valves 97, 99 may be eliminated.

Thus, the cyclonic cup's input port 60 may be fed with liquids from the supply containers 83, 87 by gravity acting in combination with the low pressure area created by the air vortex within the cyclonic cup 14 around its input port 60. Gravity fed liquids from the supply containers 83, 87 may be successfully used to supply the fog generator 34 despite their relatively low pressures because, as was described in detail earlier, the fog generator 34 does not rely on high liquid pressures or restricted nozzles in order to generate liquid fogs.

Such gravity feeding of liquids from the supply containers 83, 87 to the cyclonic cup's input port 60 and the fog generator 34 may offer the important advantages of consuming zero electrical energy; and of increasing the reliability, while reducing the cost, weight and complexity of the air sampler 10, due to the elimination of the need to use any pumps and their related valves and conduits. These important advantages may be particularly significant in the context of a human-portable air sampler 10, since lower weight is always important for human-portable devices; and since needing zero energy for pumping the liquids from the containers 83, 87 translates into lower battery weight, or into longer life for a battery of any given weight.

Whether the liquids in the containers 83, 87 are gravity fed, or pumped, the pressure in the input conduit 91 may be kept at least slightly greater than the pressure in the output conduit 69 when either of the valves 85, 89 is open, in order to prevent back flow from the conduit 69 into the conduit 91. Alternatively, such back flow may be prevented by providing a suitable check valve in the input conduit 91.

For all of their various operations that are described herein, the air pump 93, the valves 71, 73, 85 and 89, and the valve 96 described below, may be any suitable manually controlled devices. Alternatively, they may be any suitable automatically controlled devices, that are controlled by any suitable automatic control means that may adjust their operation in response to any suitable predetermined parameters.

As was described above, the main body 11 may comprise the cyclonic cup 14, the target material stripping column 16, and the demister 18; while the air inlet section 12 may comprise the air inlet tube 32 and the fog generator 34.

During operation of the air sampler 10, after the fresh water in the air inlet section 12 and the main body 11 have stripped at least some of the target material from the air passing through the air inlet section 12 and the main body 11, the water (and any stripped target material that it contains), may end up in the reservoir 53.

However, not all of the water that was introduced into the air inlet section 12 and the main body 11 may end up in the reservoir 53. This is because some water may be lost through evaporation to the air passing through the air inlet section 12 and the main body 11; and because the main body 11 may not be able to strip 100% of the water fog particles 54 from the air passing through the main body 11. In addition, as will be explained in more detail below, some of the water from the reservoir 53 may either be consumed by the detection apparatus 67, and/or dumped into the waste container 98.

Accordingly, the water level control means 55 for the reservoir 53 may serve to keep the reservoir 53's water level within predetermined lower and upper limits.

The predetermined lower limit may be selected so that the reservoir's outlet port 43 may covered with water at all times, so that air bubbles will not be fed into the output conduit 69. When the water level is at its predetermined lower limit, light from the light source in the lower light source/photodetector pair 61 may be reflected from the float 57 into its photodetector and generate an output signal, while light from the light source in the upper light source/ photodetector pair 63 may not be reflected from the float 57 into its photodetector and may not generate an output signal.

The presence of an output signal from the lower pair 61 and the absence of an output signal from the upper pair 63 may indicate to any suitable control system (that comprises part of the liquid level control means 55), that more water needs to be added to the air inlet section 12 and the main body 11. The control system may then automatically actuate one, or more, of the valves 85, 71, 73 to start the flow, or increase the flow, of fresh water from the fresh water supply container 83 into the input conduit 91.

The predetermined upper limit for the reservoir 53's water level may be selected so that the water level is slightly below the stripping column 16's top edge 65. When the water level is at its predetermined upper limit, light from the light source in the upper light source/photodetector pair 63 may be reflected from the float 57 into its photodetector and generate an output signal, while light from the light source in the lower light source/photodetector pair 61 may not be reflected from the float 57 into its photodetector and may not generate an output signal.

The presence of an output signal from the upper pair 63 and the absence of an output signal from the lower pair 61 may indicate to any suitable control system that no more fresh water needs to be added to the air inlet section 12 or the main body 11. The control system may then automatically actuate one, or more, of the valves 85, 71, 73 to stop the flow, or reduce the flow, of fresh water from the fresh water supply container 83 into the input conduit 91.

Alternatively, any other suitable liquid level control means may be used other than the liquid level control means 55 illustrated in FIG. 1.

As was explained in detail above, if there is any target material in the incoming air, at least part of the target material may be stripped from the air, and concentrated, by the water used in the air inlet section 12 and the main body 11; with the water containing the target material ending up in the reservoir 53.

A water sample from the reservoir 53 may then be provided to the detection apparatus 67 through the output conduit 69 and the sample conduit 94 by activating the sample pump 75 until the desired water sample has been obtained, at which time the sample pump 75 may then be turned off. Alternatively, the sample pump 75 may be left on if continuous sampling of the water from the reservoir 53 is desired.

The detection apparatus 67 may be any detection apparatus that is suitable for detecting the presence, amount and/or identity of the target material that is in the water sample, which may be a function of the presence, amount and/or identity of the target material that is in the air being sampled by the air sampler 10.

In some cases, the detection apparatus 67 may need to detect the presence, amount and/or the identity of the target material in the air in the shortest possible time, such as when the detection apparatus 67 is used to detect nerve gas, or is used to detect explosives in luggage or in buried land mines, for example. Accordingly, a water sample from the reservoir 53 for the detection apparatus 67 may be provided in the shortest possible time if the water travels through the air inlet section 12 and the main body 11 only once before being supplied to the detection apparatus 67. In addition, for any given flow rate of the water through the air sampler 10, the water sample from the reservoir 53 may be produced more quickly by minimizing the water flow lengths in the air inlet section 12 and the main body 11.

However, in some cases the concentration of the target material in the air entering the air inlet section 12 may be so low that the water, in only one passage through the air inlet section 12 and the main body 11, may not be able to strip enough of the target material from the incoming air to permit the detection apparatus 67 to detect the presence, amount and/or identity of the target material.

For example, let it be assumed that the target material is present in the air in a concentration of 1 part per billion; that the detection apparatus 67 can only detect concentrations of the target material that are at least 5 parts per billion; that the water in the air inlet section 12 and the main body 11 is recirculated; and that each time the water is recirculated, it can strip enough target material from the air to raise the concentration of the target material in the water by 2 parts per billion. Thus, even after two cycles through the air inlet section 12 and the main body 11, the concentration of the target material in the recirculated water will still be only 4 parts per billion, which is undetectable by the detection apparatus 67. However, after three cycles through the air inlet section and the main body 11, the concentration of the target material in the water will be raised to 6 parts per billion, which will be easily and accurately detectable by the detection apparatus 67.

In some circumstances, it may be desirable to continuously discharge into the waste container 98 a preset fraction of the water circulating through the air inlet section 12 and the main body 11, and to continuously replace that discharged water with fresh water from the supply container 83. This may be desirable because it may, over a period of time, permit the water in the air inlet section 12 and the main body 11 to clear itself of any old, historical target material that may have been stripped from the incoming air in the past, and permit the water in the air inlet section 12 and the main body 11 to strip new target material from the new incoming air.

Such gradual clearing of any old, historical target material from the water in the air inlet section 12 and the main body 11 may be important in any situation where it is desired that the detection apparatus 67 detect target material that is currently entering the air sampler 10, rather than target material that has entered it in the past. This is because the type and/or amount of the target material entering the air sampler 10 may change with time and/or the location of the air sampler 10.

From the forgoing description of the fluidic circuitry 22, it will now be apparent to those skilled in the art how to utilize it, for example, to supply the detection apparatus 67 with samples of the water from the reservoir 53 that has passed once, or more than once, through the air inlet section 12 and main body 11; to provide the samples continuously, or in any desired number, volume and timing, within reason; and to provide fresh water and cleaning liquid to the main body 11 and air inlet section 12.

It should also be understood that the forgoing fluidic circuitry 22 was only described by way of non-limiting example, since the air sampler's air inlet section 12 and/or main body 11 may be utilized with any of a nearly infinite variety of other suitable fluidic circuits, depending on the tastes and needs of the user.

Maximizing the Air/water Ratio in the Main Body 11:

The air/water ratio in the main body 11 may be either the ratio of the volume of air passing through the main body 11 to the volume of water passing through main body 11, or the ratio of the volume of air passing through the main body 11 to the volume of water residing in the main body 11 at any one time. It is clear that maximizing either, or both, of these air/water ratios may have a dramatic, positive effect on the concentration of the stripped target material in a water sample provided by the main body 11.

This is because, in general, each time the water passes through the main body 11 (i.e., through the cyclonic cup 14, the stripping column 16 and the demister 18), it will be able to strip only a certain amount of the target material from the air. Thus, as the amount of the water used in the main body 11 gets smaller and smaller, the greater and greater will be the concentration of that stripped target material in the water. Naturally, the amount of water used in the main body 11 must not be reduced to the point that the main body 11 will no longer be able to operate in its intended fashion.

Since modern detection apparatus 67 may operate with water samples as small as about 1 cc, or less, using minimal amounts of water in the main body 11 may not prevent the proper operation of the detection apparatus 67; and the increased concentration of the target material in the water sample may enable the detection apparatus 67 to accurately detect the presence, amount and/or identity of the target material at the earliest possible time.

The benefit of maximizing the air/water ratio in the main body 11, may be demonstrated with the first-order sampler model shown in FIG. 7. During operation of the sampler model, it may be assumed that a continuous flow of air 102, at the rate of $\dot{N}_a$ moles/sec, and a continuous flow of fresh water 104, at the rate of $\dot{V}_w$, may enter an air-to-water mass transfer device 100 holding a volume $V_w$ of the water 104.

It may also be assumed that the air 102 entering the mass transfer device 100 may contain the target material 106 at a small mole fraction $x_{t0}$; while the fresh water 104 entering the mass transfer device 100 may contain no target material 106. As the air 102 passes through the mass transfer device 100, some of the target material 106 that it carries may be stripped from the air 102 by the water 104 so that the air 102 exiting from the mass transfer device 100 may carry a lower mole fraction of the target material 106 $x_{t1}$.

It may be further assumed saturation of the water 104 with the target material 106 may not occur.

Accordingly, conservation of the target material 106 may yield the following equation for the concentration $C_t$ of the target material 106 in the water 104 exiting the mass transfer device 100 as a function of time:

$$C_t = \frac{(x_{t0} - x_{t1})\dot{N}_a}{\dot{V}_w} \cdot \left[1 - \exp\left(\frac{-\dot{V}_w t}{V_w}\right)\right] \quad (6)$$

where t is the elapsed time as measured from the initial entry of the air 102 carrying the target material 106 into the mass transfer device 100.

The above model shows that for fixed flow rates of air 102 and water 104 into the mass transfer device 100 the concentration of the target material 106 in the water 104 as it exits the mass transfer device 100 may be exponentially dependent, in inverse form, on the volume of the water 104 within the mass transfer device 100 at any one time, as long as the volume of water 104 is not reduced to the point that the mass transfer device 100 does not function properly as, for example, in a wetted wall cyclonic cup 14 whose internal surfaces 58, 72 are not uniformly wetted by the water 104.

The above model also shows that for a fixed flow rate of the air 102 through the mass transfer device 100 and for a fixed volume of the water 104 in the mass transfer device 100, the concentration of the target material 106 in the water 104 as it exits the mass transfer device 100 may be inversely proportional to the flow rate of the water 104 entering and exiting the mass transfer device 100, as long as the volume of water 104 in the mass transfer device 100 is not reduced to the point that the inner surface of the mass transfer device 100 is no longer entirely covered by the water 104.

This may be because: (a) the slower the flow rate of the water 104 into the mass transfer device 100, the longer the water 104's dwell time within the mass transfer device 100; (b) the longer the dwell time, the greater the amount of target material 106 that the water may strip from the air 102; and (c) the greater the amount of stripped target material 106, the greater the concentration of the target material 106 in the water 104 exiting the mass transfer device 100.

The above model further shows that the concentration of the target material 106 in the water 104 as it exits the mass transfer device 100 may be proportional to the flow rate of the air 102 through the mass transfer device 100.

In order to illustrate the above model, consider the specific case of detecting the vapors from the high explosive RDX, which has a vapor pressure at 30° C. of $5.8(10^{-8})$ mmHg. Assume a partial pressure for RDX that is 60% of the saturation value, i.e. a mole fraction in air of about 46 ppt (parts per trillion). Also assume a flow rate of 283 LPM (liters per minute) for the air 102 in the mass transfer device 100; a liquid volume of 1 cc for the water 104 in the mass transfer device 100; a flow rate of 1 cc/min (cubic centimeter per minute) for the water 104 through the mass transfer device 100; and a stripping efficiency of 83% for the water 104 at stripping the RDX vapors from the air 102.

Referring now to FIG. 8, the curve 108 shows the time-varying concentration of the RDX vapors in the water 104 exiting the mass transfer device 100 in ppb (parts per billion) by weight. The curve 108 shows that within 10 seconds the concentration of RDX vapors in the exiting water 104 has reached about 16 ppb, a concentration that is well above the present 1–2 ppb detection limit for state of the art immunoassay detection apparatus 67.

Accordingly, the above model demonstrates that very low concentrations of vapors from explosives, like RDX vapors, may be detected in pseudo real-time by using the main body 11 to supply the samples to the detection apparatus 67, if (a) comparatively fast flows of large volumes of air through the main body 11 are combined with (b) small liquid volumes of water that (i) have a large surface area and (ii) a high recirculation rate through the mass transfer device 100 (i.e., are recirculated repeatedly through the mass transfer device 100).

On the other hand, where time is not of the essence, the concentration of the target material in the water in main body 11 may be further increased by (a) reducing the flow rate of the water through the main body 11 (i.e., by increasing its dwell time within the main body 11); and/or by recycling the water through the main body 11 more than once.

Example Specifications for the Air Samoler 10 of FIGS. 1–8:

By way of non-limiting example, the air sampler 10 may have the following specifications.

The main body 11 may have an air/water ratio of the volume of air passing through the main body 11 in a given amount of time to the volume of water passing through main body 11 during that given amount of time of at least about 10,000:1.

The main body 11 may have an air/water ratio of the volume of air passing through the main body 11 in a given amount of time to the volume of water residing in main body 11 during that given amount of time of at least about 10,000:1.

The main body 11 may hold a volume of air of about 250 cc. Air flow into the main body 11 may be about 250 LPM (liters per minute); and may have velocities in the range of about 0.4 to more than 1.0 m/sec (meters per second). The dwell time of the air in the main body 11 may be about 0.1 seconds.

The main body 11 may hold a liquid volume of stripping water (not including any water in the reservoir 53), in the range of about 1 to 10 cc. Water flows of the stripping water through the main body 11 may be in the range of about 3 to 20 cc/min. The area of the cyclonic cup's wetted inner surface 58 may be about 20 $cm^2$ (square centimeters); the area of the cyclonic cup's wetted inner surface 72 may be about 40 $cm^2$; the area of the stripping column's wetted inner surface 82 may be about 70 $cm^2$; and the area of the demister's wetted inner surface 49 may be about 130 $cm^2$.

The stripping water for the main body 11 may be provided in the form of water fog particles 54 from the fog generator 34 and in the form of liquid water from the cyclonic cup's input port 60.

If a fog generator 34 is used, the water fog particles 54 may have diameters in the range of about 10 to 20 microns. However, these may not be the optimum sizes of the water fog particles 54 for all situations, since the optimum size(s) of the water fog particles 54 may vary with the particular sizing and physical construction of the air sampler's main body 11 and air inlet section 12, and may also vary with the nature of the particular target material under consideration.

Whether or not a fog generator 34 is located in the air inlet tube 32, the air inlet tube 32 may have a length in the range of about 1 to 10 cm, and a cross-sectional area in the range of about 5 to 25 $cm^2$.

The cyclonic cup's air chamber 76 may have a diameter of about 4.6 cm and a height of about 2.5 cm.

The stripping column's air chamber 84 may have a diameter of about 2.5 cm and a height of about 10 cm. The number of grooves 88 and bosses 90 in the stripping column 16 may be in the range of about 0.5 to 5 grooves per centimeter of height of the stripping column 16. Each groove 88 may have a depth of about 1.5 mm, and a width in the range of about 2 to 20 mm. Each boss 90 may have a width of about 1.5 mm. As was explained above in detail, preferably the grooves 88 and bosses 90 may have the same handedness as the air vortex within the stripping column 16.

The demister's air chamber 164 may have a diameter in the range of about 3.8 to 4.6 cm, and a height of about 10 cm. However, it may be noted that for any given flow rate of air through the air chamber 164, if its diameter is made too large, any remaining water fog particles 54 may not be as efficiently swept by the air chamber 164's rotating air vortex into its sidewall 47 and its reservoir 53. If its diameter is made too small, then some, or all, of the remaining water fog particles 54 may be lost by being swept by its air vortex out of the demister 18.

Turning now to other matters, the air sampler's main body 11 and the air inlet section 12 may, as illustrated in FIG. 1, comprise a number of discrete parts (i.e., the air inlet tube 32, cyclonic cup 14, stripping column 16 and demister 18). Those discrete parts may be fabricated in any suitable way, such as by machining or molding, and may assembled together in any suitable way, such as by the use of friction fits, threaded fits, and/or adhesives. Alternatively, two, or more, of those discrete parts may be fabricated as one integral piece in any suitable way, and then assembled together with the remaining discrete part(s) in any suitable way. Alternatively, all of those discrete parts may be fabricated as one integral piece.

As seen in FIG. 1, there are many right angle corners in the air sampler 10's main body 11, e.g., between the cyclonic cup 14's base 58 and sidewall 70, between the cyclonic cup 14's sidewall 70 and cover 62, between the grooves 88 and the bosses 90 in the stripping column 16, between the stripping column 16 and the demister 18's base 41, and between the demister 18's base 41 and sidewall 47. Such corners may present a problem since they may provide hard to clean traps for the stripping and cleaning liquids used in the air sampler 10. Such traps may be undesirable since they may cause the air sampler 10 to give spurious results under certain circumstances.

Accordingly, as a further alternative to the air sampler 10 of FIG. 1, any, or all, of the right angle corners in its main body 11 may be replaced by a smoothly curved fillet, in order to avoid the formation of such undesirable traps.

MAINTAINING A CONSTANT VOLUME OF WATER IN THE AIR SAMPLER'S MAIN BODY 11:

Most, if not all, conventional air sampler devices are batch devices in which the stripping liquid passes through the device only once. Thus, such devices do not have an ability to maintain a constant volume of stripping liquid (such as water) in the device. Accordingly, it is also not possible for such devices to, for example, provide continuous stripping of the target material from the air, which may otherwise increase the concentration of the target material in that constant volume of stripping liquid.

As used herein, the term "constant volume" means that the volume is maintained within pre-determined lower and upper limits. of course, the pre-determined lower and upper limits may be identical if the volume is to be maintained at one fixed quantity.

However, continuous stripping of the target material from the air by a recycled, fixed volume of stripping liquid may be very important such as, for example, where the concentration of the target material in the air is so low that it is not possible to strip a detectable amount of the target material from the air with a single batch of stripping liquid that passes through the air sampler only once.

Accordingly, one of the features of the air sampler 10 may be that it comprises a constant volume means. The constant volume means may be, of course, for recycling the water through the air sampler's main body 11, and for maintaining a constant volume of water in the air sampler's main body 11. For any given stripping liquid, such as water, maintaining a constant volume is essentially the same as maintaining a constant weight of that stripping liquid.

For example, with respect to the air sampler 10 of FIG. 1, such constant volume means may comprise the reservoir 53 and the output conduit 69, which may collect and recycle the water (and any stripped target material that it may carry) through the air sampler's main body 11 at least once. As has been described, such recycling may be enabled, or assisted, by gravity feed and/or by the low pressure area created by the cyclonic cup 14's air vortex around the input port 60. Such a constant volume means may further comprise the float-type liquid level control means 55 for detecting when the volume of the water in the reservoir 53 reaches a pre-determined minimum, and for adding water to the main body 11 from the fresh water supply container 83 (and its related conduit 91). Similar comments may apply to the constant volume means of the air sampler 130 of FIG. 9, which may comprise the reservoir 53a, the output conduit 69a, the liquid level control means 55a and the fresh water supply container 83 (and its related conduit 91a).

Figure 12:
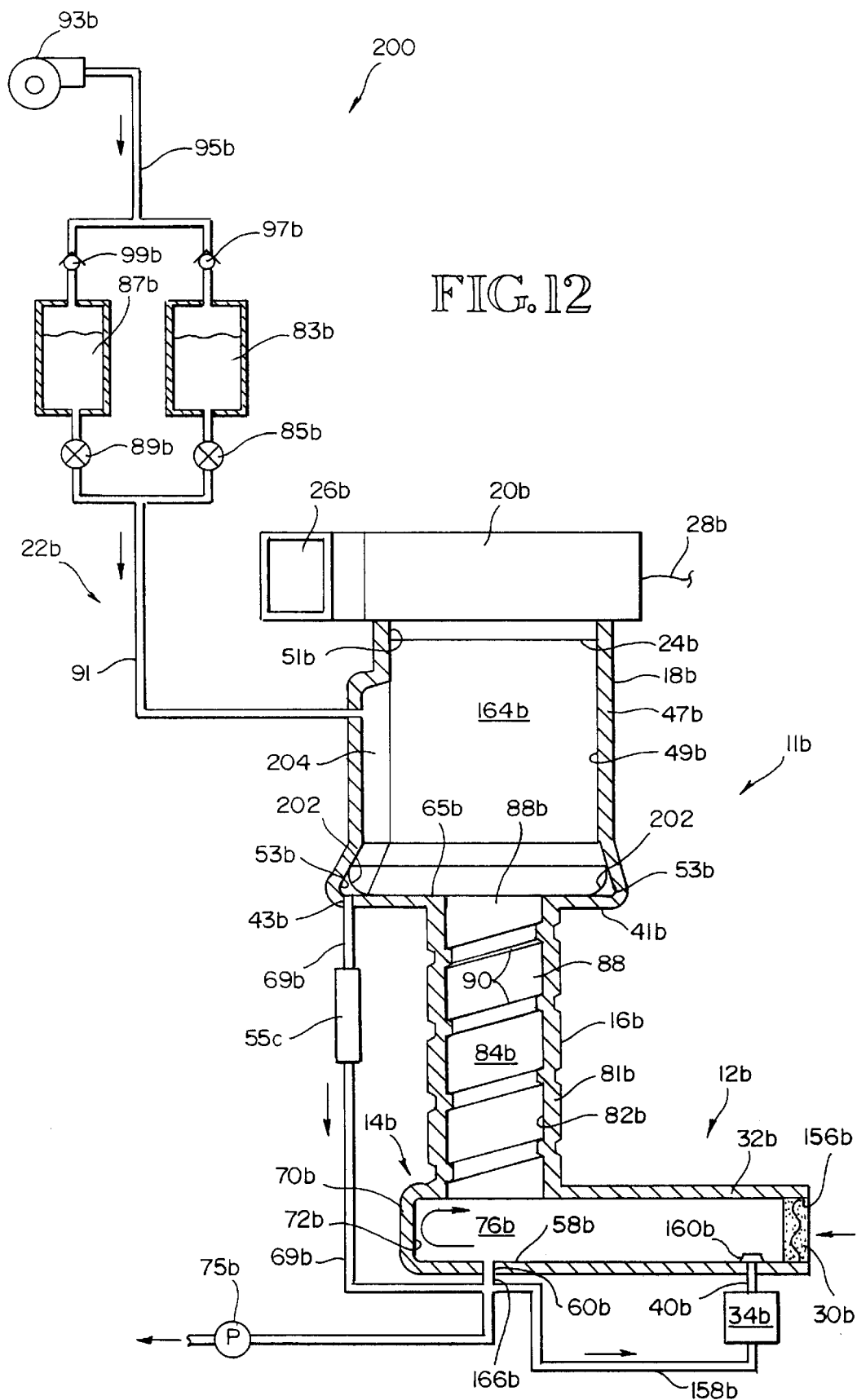
FIG. 12 is a diagrammatic view, partly in elevation and partly in cross-section, of the high efficiency, wetted surface, cyclonic air sampler 200 of the present invention.

With respect to the air sampler 12 of FIG. 12, such constant volume means may comprise the reservoir 53b, and the output conduit 69b, which may collect and recycle the water (and any stripped target material that it may carry) through the air sampler's main body 11b at least twice. As has been described, such recycling may be enabled, or assisted, by gravity feed and/or by the low pressure area created by the cyclonic cup 14b's air vortex around the input port 60b. Such a constant volume means may further comprise the capacitance-type liquid level control means 55b of FIG. 13 for monitoring the thin film of water in the stripping column 16b; or the optical-type bubble detector 55c (seen in FIG. 12) for the output conduit 55b; as well as the fresh water supply container 83b (and its related conduit 91b).

Alternatively, the liquid level control means 55, 55a, 55b and 55c may comprise:

(a) any conventional pressure gauge for measuring the gauge pressure, or fluctuations thereof, of the water in the reservoir 53, 53a and 53b, and/or in the output conduit 69, 69a, and 69b;

(b) any conventional temperature sensor for monitoring the heat loss or temperature of any conventional heated element placed in the water flowing through the output conduit 69, 69a and 69b;

(c) any conventional optical or acoustical sensor for monitoring the velocity of the water (and/or the velocity of any particles carried by the water) in the output conduit 69, 69a and 69b;

(d) any conventional acoustical sensor for measuring changes in the acoustic impedance of the water in the output conduit 69, 69a and 69b due to flow conditions of that water;

(e) any conventional acoustical sensor for measuring the turbulence noise of the water flowing through the output conduit 69, 69a and 69b;

(f) any conventional sensor for measuring any other measurable property of the water flowing through the output conduit 69, 69a and 69b that will change with the flow rate of that water; and/or (g) any conventional sensor for measuring the thickness of the water film on any portion of any of the inner surfaces of the main body 11, 11a, 11b, such as determined by: (1) the optical waveguiding changes in any transparent or translucent wall of the main body 11, 11a, 11b caused by the index of refraction difference between a liquid or an air "coating" on that wall; (2) an acoustic echo technique that monitors the thickness of the water film or the acoustic impedance at an interface, which would be different if the inner surface were wet or not; (3) a heated wire temperature device at the surface of the water film; and/or (3) a sensor for monitoring any change in the electromagnetic coupling (such as the dielectric constant) of the water film that is affected by the presence, thickness or absence of the water film such as a radar technique, a capacitor or a transformer.

All of the forgoing constant volume means may also be used with the air sampler 130 of FIG. 9 and the air sampler 200 of FIG.

THE HIGH EFFICIENCY, WETTED SURFACE CYCLONIC AIR SAMPLER 200, HAVING A ONE-PIECE MAIN BODY 11B AND AIR INLET SECTION 12B

Turning now to FIG. 12, it illustrates the high efficiency, wetted surface, cyclonic air sampler 200 of the present invention. The air sampler 200 may be simpler, and better, in certain respects as compared to the air sampler 10 of FIGS. 1–8. This is because, for example, as will be described in more detail below, the air sampler 200's main body 11b may be formed as one integral piece having no fluid trapping right angle corners formed by its internal intersecting surfaces, such as the internal intersecting surfaces of the cyclonic cup 14b, the stripping column 16b and the demister 18b. In addition, the air sampler 200's air inlet section 12b may be formed as one integral piece with its main body 11b.

Nevertheless, the air sampler 200 may be the same as, or at least similar to, the air sampler 10 of FIGS. 1–8 with respect to all aspects of its theory, construction and operation, except for those differences which will be made apparent by all of the disclosures herein.

Accordingly, for clarity and simplicity, certain parts of the air sampler 200 of FIG. 12 have been given the same reference numerals, with an "b" appended, as the reference numerals used for the corresponding respective parts of the air sampler 10 of FIGS. 1–8.

Turning now to FIG. 12, the air sampler 200 may comprise a main body 11b, an air inlet section 12b, and a fan 20b for urging air through the main body 11b and air inlet section 12b. Although not illustrated in FIG. 12, for clarity, the fog generating slot 168 or the spiral fog generating nozzle 170 of the air sampler 10 of FIG. 1 may be used in conjunction with the water input port 60b of the cyclonic cup 14b of the air sampler 200 of FIG. 12.

The air sampler 200 may further comprise fluidic circuitry 22b. The fluidic circuitry 22b may be designed for multiple functions such as, for example, supplying water to the main body 11b and/or to the air inlet section 12b; supplying cleaning liquid to the main body 11b and/or the air inlet section 12b; removing samples of the water (which may carry stripped target material) from the main body 11b; removing waste liquid from the main body 11b; and/or detecting the presence, amount and/or identity of the target material in the samples of the water. The fluidic circuitry 22b may include a pump 75b for removing samples and/or waste delivered to it by the reservoir 53b's output conduit 69b.

The output conduit 69b and the input conduits 158b, 166b may, as seen in FIG. 12, provide unrestricted passage of the water from the reservoir 53b to the input port 60b and/or the fog generator 34b, i.e., no flow control valve is used to control the flow of water from the reservoir 53b to the input port 60b and/or the fog generator 34b. This may be desirable since it may increase the water recirculation rates through the main body 11b by a factor of about 2 to 5 times, as compared to the fluidic circuitry 22 of the air sampler 10 of FIG. 1, thereby improving the response of the air sampler 200, as compared to the air sampler 10. This may also be desirable since the lack of flow control valve(s) in the output conduit 69b and the input conduits 158b, 166b, eliminates the cleaning and/or clogging problems that such flow control valves 71, 73 and/or 96 may cause in the fluidic circuitry 22 of the air sampler 10 of FIG. 1. However, as an alternative, one or more flow control valves may be used in the output conduit 69b, the input conduit 158b, and/or the input conduit 166b.

If only the fog generator 34b is used to supply water to the air inlet tube 32b and the main body 11b, then the cyclonic cup 14b's inlet port 60b may be eliminated. Similarly, if only the cyclonic cup 14b's inlet port 60b is used to supply water to the main body 11b, then the fog generator 34b and the air inlet tube 32b may be eliminated. If both the fog generator 34b and the inlet port 60b are used, then any suitable valves may be used in their respective input conduits 166b, 158b to regulate the respective proportions of the water that the fog generator 34b and the inlet port 60b supply.

The fluidic circuitry 22 of the air sampler 10 (FIG. 1) or the fluidic circuitry 22a of the air sampler 130 (FIG. 9) may be used in lieu of the fluidic circuitry 22b of the air sampler 200 (FIG. 12); and the fluidic circuitry 22b of the air sampler 200 may be used in lieu of the fluidic circuitry 22 of the air sampler 10 or the fluidic circuitry 22a of the air sampler 130. Any modifications to the air samplers 10, 130 and/or 200 that may be needed to effectuate these changes will be readily apparent to those skilled in the art, in view of all of the disclosures herein.

As seen in FIG. 12, the air inlet tube 32b and the main body 11b (including the cyclonic cup 14b, the stripping column 16b and the demister 18b) may all be made as one integral piece. This may be done in any suitable way, such as by blow-molding or by roto-molding. The air inlet tube 32b and the main body 11b may be made from any suitable material, such as the polymers cellulose acetate butyrate, polycarbonate or PETG.

In a blow molding process a tubular preform may be placed into a two-piece, heated, split-shell female mold that represents the external shape of the desired main body 11b and air inlet tube 32b. Once the preform has reached its softening point, pneumatic pressure may be applied to its interior, causing the preform to bulge out and assume the mold's interior shape. After cooling, the finished integral main body 11b and air inlet tube 32b may be removed from the mold. Alternatively, only the main body 11b may be blow molded, and the air inlet tube 32b may be a separate part that may then be secured to the main body 12b in any suitable way.

Roto-molding is similar to blow-molding except that the heated, two-part, female mold is charged with a small amount of granular polymer, which melts and coats the mold's interior while the mold is rotated. After cooling, the finished integral main body 11b and air inlet tube 32b may be removed from the mold. Alternatively, only the main body 11b may be roto-molded, and the air inlet tube 32b may be a separate part that may then be secured to the main body 12b in any suitable way.

Both molding techniques may offer at least the following advantages: (a) lower cost and greater uniformity, as compared to manufacturing separate parts which are then assembled together; (b) the internal surfaces of the main body 11b and the air inlet tube 32b may automatically form exceedingly smooth internal surfaces during the molding process, for better flow of the incoming air through the air inlet tube 32b, and for better flow of the air and the thin water film across the internal surfaces of the main body 11b; and (c) the internal surfaces of the main body 11b and the air inlet tube 32b may automatically form smoothly curved internal fillets during the molding process between intersecting surfaces (such as between the cyclonic cup 14b's base 58b and sidewall 70b), thereby avoiding undesired water traps, and assisting better flow of the air and/or the thin water film over such intersecting surfaces.

It has been discovered that it may be very important for the internal surfaces of the main body 11b to be wettable, or hydrophilic. The importance of this, and the manner of doing this, are at least similar to, if not the same as, the importance and manner of doing that were explained above regarding the inner surfaces 58, 72 of the air sampler 10's cyclonic cup 14, and thus need not be repeated here.

As was the case with the main body 11 of FIG. 1, during operation of the main body 11b of FIG. 12 a thin water film flows across the internal surfaces of the cyclonic cup 14b and the stripping column 16b, before flowing into the demister 18b. However, it has been discovered that the air vortex within the demister 18b swirls the incoming water from the stripping column 16b, and propels it to circulate within the demister 18b as a triangular shaped water fillet 202 within the annular reservoir 53b that may be formed at the intersection between the demister's base 41b and sidewall 47b. Although the annular reservoir 53b is illustrated as comprising a flared portion of the bottom of the demister 18b, such a flair may be eliminated, in which case the annular reservoir 53b may comprise the intersection between the demister's non-flared base 41b and sidewall 47b.

Thus, it is seen that the demister 18b needs no separate inner wall to prevent its water 202 from flowing back into the stripping column 16b, since the demister 18b ingeniously uses the air vortex within the demister 18b to eliminate the need for such an inner wall. This not only desirably simplifies the demister 18b, but that very simplicity offers the additional benefit of eliminating another set of intersecting surfaces which might otherwise act as a hard to clean water trap. Compare the reservoir 53 of the demister 18 of FIG. 1, where the portion of the sidewall 81 of stripping column 16 that protrudes into the demister 18 is needed to form the inner wall of its reservoir 53, and may form a hard to clean intersecting surface with the demister 53's base 41.

Since the reservoir 53b holds a much smaller volume of water than the reservoir 53, this may permit a desirable reduction in the total water inventory needed for the optimum operation of the air sampler 200, as compared to the air sampler 10.

As is seen in FIG. 12, the demister 18b may also be provided with a vertically extending gutter 204 in its sidewall 47b. The air vortex within the demister 18b may cause the water film on its inner surface 49b to circulate in a spiral pattern. When the water film encounters the vertically extending gutter 204, the air vortex may urge it to flow into the vertically extending gutter 204, where the force of gravity may then urge the accumulating water in the vertically extending gutter 204 to flow down into the reservoir 53b. The term "vertically extending" as used herein with respect to the gutter 204 is to be understood to include any gutter 204 (whether linear or not), that has one portion higher than another portion with respect to the demister's base 41b; such as, for example, a diagonal gutter 204 tilted at an angle with respect to the vertical axis of the demister 18b. A vertically extending gutter 204 may also be provided for the demister 18 of the air sampler 10 of FIG. 1.

As seen in FIG. 12, no float-type liquid level control means 55 (like that used by the air sampler 10 of FIG. 1) may be needed as part of the air sampler 200, since the demister 11b does not have (or need) the large capacity reservoir 53 of the air sampler 10. This may be desirable since such a liquid level control means 55 may be hard to clean, and may fail by sticking or jamming.

Figure 13:
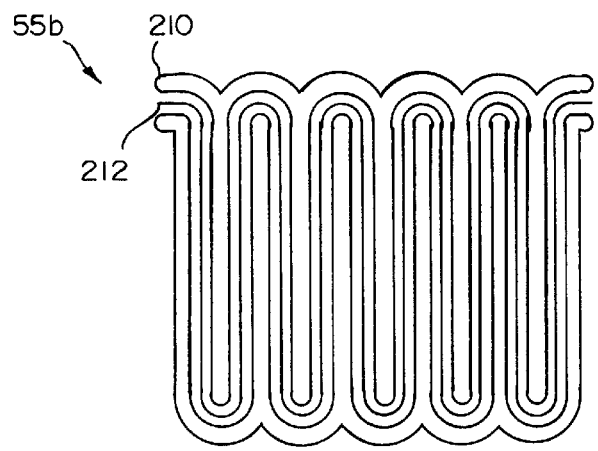
FIG. 13 is top elevational view of a capacitance-based liquid level control 55b.

Instead, the air sampler 200 of FIG. 12 may comprise the dual electrodes 210, 212 capacitance-based liquid level control means 55b that is illustrated in FIG. 13, which may be used to sense the thickness of the film of water on the internal surface 82b of the stripping column 16b. The conductive electrodes 210, 212 may be formed on any suitable flexible substrate, such as a plastic substrate, by any suitable technique, such as any conventional printed circuit-type techniques. The pattern of the electrodes 210, 212 that is illustrated in FIG. 13 is shown only by way of non-limiting example, since a wide variety of other suitable patterns for the electrodes 210, 212 will now occur to those skilled in the art, in view of all of the disclosures herein. The substrate bearing the electrodes 210, 212 may then be wrapped around, and secured to the stripping column 16*b*. By way of example, if the stripping column 16*b* has an external area of 150 cm$^2$, then the area of the pattern of electrodes 210, 212 may be about 75 cm$^2$, although it may be larger or smaller. During operation, the electrodes 210, 212 create a "fringing field" between themselves that may represent up to ⅓ of the total plate to plate capacitance of the electrodes 210, 212. When the film of water on the internal surface 82*b* of the stripping column 16*b* enters the fringing field, the plate to plate capacitance of the electrodes 210, 212 increases markedly, since the dielectric constant of water is about 80, while that of air is 1.0 and that of the stripping column 16*b*'s sidewall 81*b* may be in the range of about 3–4.

The electrodes 210, 212 may be connected to any suitable electronic control module (not illustrated, for clarity), which may provide them with a suitable voltage and which may sense any changes in their plate to plate capacitance by any suitable means, such as by an oscillator circuit that changes frequency as their plate to plate capacitance changes. The electronic control module may then control the amount of fresh water provided to the main body 11*b* or the fog generator 34 from the fresh water supply container 83*b*, by suitably controlling the control valve 85*b*.

Since the capacitance-based liquid level control means 55*b* is located on the exterior of the stripping column 16*b*, it inherently presents no cleaning or jamming problems for the air sampler 200.

As an alternative to the liquid level control means 55*b*, the liquid level control means 55*c* seen in FIG. 12 may be utilized. The liquid level control means 55*c* may comprise a light source/photodiode pair, like the light source/photodiode pairs 61, 63 used in the liquid level control means 55 of the air sampler 10 of FIG. 1.

The flow of the water from the reservoir 53 through the output conduit 69*b* may be characterized as "bubbly", since during normal operation of the air sampler 200, there may not be sufficient water in the reservoir 53 to keep the output conduit 69*b* filled at all times. It has been discovered, by empirical tests, that the total amount of water in the main body 11*b* may have a monotonic and inverse relationship with the void fraction (represented by the bubbles) in the flow of water through the output conduit 69*b*. Accordingly, the light source/photodiode pair in the liquid level control means 55*c* may be arranged to monitor the flow of the bubbles through the output conduit 69*b*, and generate an electrical signal that fluctuates as bubbles pass by.

The light source/photodiode pair in the liquid level control means 55*c* may be connected to any suitable electronic control module (not illustrated, for clarity), which may provide them with suitable power, and which may sense the fluctuating electrical signal that they generate. The electronic control module may then perform any suitable signal processing functions, such as signal averaging functions, and any needed numerical calculations; and then suitably control the fresh water provided to the main body 11*b* or the fog generator 34 from the fresh water supply container 83*b*, by suitably controlling the control valve 85*b*.

Since the level control means 55*c* is located on the exterior of the output conduit 69*b*, it inherently presents no cleaning or jamming problems for the air sampler 200.

THE HIGH EFFICIENCY, WETTED SURFACE CYCLONIC AIR SAMPLER 130 HAVING AN INTERNAL AIR IMPELLER 140

Figure 10:
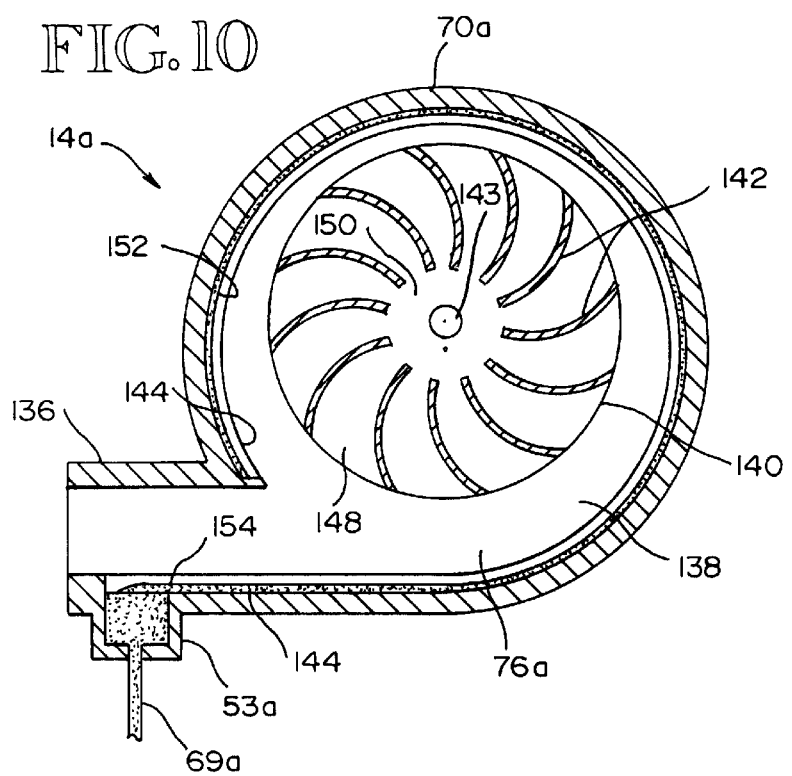
FIG. 10 is a cross-sectional view taken along line 10—10 of FIG. 9.
Figure 11:
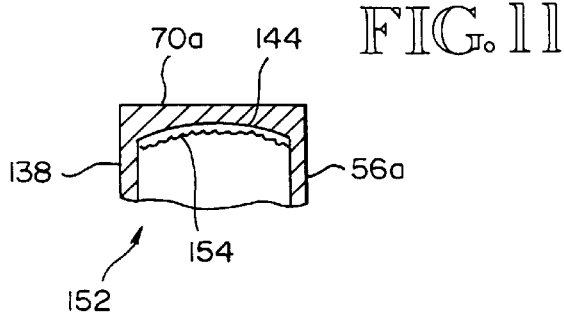
FIG. 11 is a cross-sectional view taken along line 11—11 of FIG. 9.

Turning now to FIGS. 9–11, they illustrate the high efficiency, wetted surface, cyclonic air sampler 130 of the present invention. The air sampler 130 may be simpler in certain respects, and may have a smaller size and weight, as compared to the air sampler 10 of FIGS. 1–8. This is because, as will be described in more detail below, the air sampler 130's main body 11*a* may integrate into one unit some, or all, of the functions of the air sampler 10's separate fan 20, cyclonic cup 14, stripping column 16 and demister 18.

Nevertheless, the air sampler 130 may be the same as, or at least similar to, the air sampler 10 of FIGS. 1–8 with respect to all aspects of its theory, construction and operation, except for those differences which will be made apparent by all of the disclosures herein.

Accordingly, for clarity and simplicity, certain parts of the air sampler 130 of FIGS. 9–11 have been given the same reference numerals, with an "a" appended, as the reference numerals used for the corresponding respective parts of the air sampler 10 of FIGS. 1–8.

Turning now to FIG. 9, the air sampler 130 may comprise an air inlet section 12*a*, a main body 11*a*, and an air outlet section 132. The air sampler 130 may further comprise fluidic circuitry 22*a*. The fluidic circuitry 22*a* may be designed for multiple functions such as, for example, supplying water to the main body 11*a* and/or to the air inlet section 12*a*; supplying cleaning liquid to the main body 11*a*, the air inlet section 12*a*, and/or the air outlet section 132; removing samples of the water (which may carry stripped target material) from the air outlet section 132; removing waste liquid from the main body 11*a*, the air inlet section 12*a* and the air outlet section 132; and/or detecting the presence, amount and/or identity of the target material in the samples of the water.

The main body 11*a* may comprise a cyclonic cup 14*a*. The air outlet section 132 may comprise an air outlet tube 136 and a reservoir 53*a*. In general, the relatively high air flow through the cyclonic cup 14*a* may have the desirable effect of increasing the concentration of the target material in the water, due to the relatively large amount of the water that may be evaporated by the air flow while the water is passing through the cyclonic cup 14*a*. To aid in such an evaporation-concentration effect, the stripping liquid may comprise liquids having a volatility substantially greater than that of water, such as an alcohol or other organic liquid.

The air inlet section 12*a* may comprise an air inlet tube 32*a*, an air filter 30*a*, a fog generator 34*a*, and a fluid input conduit 146. The air filter 30*a*, the fog generator 34*a*, and the input conduit 146 may be mounted in the air inlet tube 32*a*. There may be more than one input conduit 146. Although the outlet of the input conduit 146 is illustrated as being centered in cyclonic cup's air inlet 74*a*, it may be located anywhere in the air inlet 74*a*, the air impeller's air inlet 150, or the air inlet tube 32*a*.

The fluidic circuitry 22*a* may comprise an output conduit 69*a*, an output pump 134, a cyclonic cup valve 71*a*, cyclonic cup conduits 166*a* and 146, a fog generator valve 73*a*, and fog generator conduit 158*a*. The output pump 134 may be located at any suitable location in the reservoir 53*a* or the output conduit 69*a*. When the output pump 134 is activated, the output conduit 69*a* may convey water from the reservoir 53*a* (which may carry stripped target material), to the cyclonic cup 14*a* through the cyclonic cup valve 71*a* and conduits 166*a* and 146; and/or to the fog generator 34*a* through the fog generator valve 73*a* and conduit 158*a*.

The fluidic circuitry 22a may further comprise a sample conduit 94a, a sample pump 75a, a detection apparatus 67a, a valve 96a, a waste conduit 77a, a waste pump 79a and a waste container 98a. Samples of the water from the reservoir 53 (which may carry stripped target material) may be supplied to the detection apparatus 67a through the conduits 69a and 94a by surfaces to stream outwardly over those internal surfaces towards its periphery, from which the thin water film may then be flung at a high velocity, in the form of a spray of fine water droplets, against the inner surface 144 of the cyclonic cup's sidewall 70a, where the water droplets may then coalesce back into a film of water 154.

The rapidly spinning air impeller 140 may also expel the air from its periphery at high velocity, and thus also fling any water entrained in the air and any remaining water fog particles 54a against the sidewall's inner surface 144 at a high velocity, where they may be coalesced into a film of water 154.

As best seen in FIG. 11, the cyclonic cup 14a's sidewall 70a and end walls 56a, 138 may form a collection trough 152 for the water 154. As best seen in FIG. 10, the air expelled from the rapidly spinning air impeller 140 may move in a clockwise direction in the cyclonic cup's air chamber 76a, thereby "pumping" the water 154 in a clockwise direction through the collection trough 152 and into the reservoir 53a.

As seen in FIG. 11, in order to maximize the surface area of the water 154 in the trough 152, the sidewall's inner surface 144 may have a curved shape that may be selected to permit the water to have an uniform depth over the inner surface 144. Maximizing the surface area of the water 154 may be important because the amount of target material that may be stripped by the water 154 from the air passing over it may be proportional to the surface area of the water 154.

It may be that the maximum surface area of the water 154 may be obtained when the surface area of the inner surface 144 is selected to equal the surface area of the thinnest unbroken water film 154 that can be maintained over the inner surface 144. The thinnest unbroken water film 154 that can be maintained over the inner surface 144 may be governed by such considerations as the velocity of the air passing over the water 154 in the trough 152; the area of the inner surface 144; and/or the velocity, total liquid volume, and/or replenishment rate of the water 154 in the trough 152.

Figure 11A:
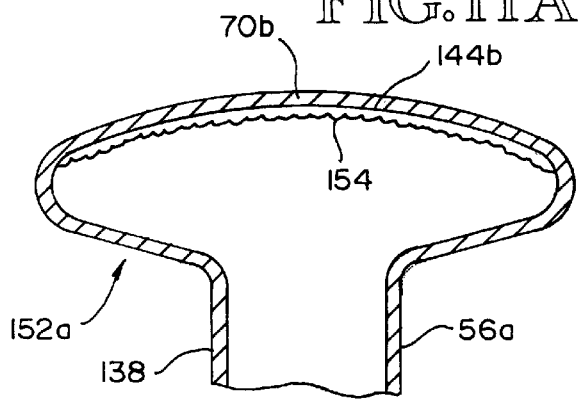
FIG. 11A is a cross-sectional view of an alternative embodiment of the air sampler 130, similar to that of FIG. 11.

Referring now to the alternative embodiment of the cyclonic cup 14a seen in FIG. 11a, the cyclonic cup 14a may comprise an alternative trough 152a comprising the end walls 56a, 138 and an enlarged sidewall 70b having a generally C-shaped cross-section. As seen, the enlarged sidewall 70b may provide an enlarged inner surface 144b for the water 154, which may help in maximizing the surface area of the water 154.

Alternatively, the sidewall's inner surface 144, 144b may have any other shape, and the water 154 may not be of uniform depth over the inner surface 144, 144b. Alternatively, the trough 152, 152a may be formed entirely by the cyclonic cup's end wall 70a, 70b, such as by providing an end wall 70a, 70b having a U-shaped or a V-shaped cross-section.

It has been discovered that it may be very important for the air impeller 140's internal surfaces, and/or the sidewall's inner surfaces 144, 144b to be wettable, or hydrophilic. The importance of this, and the manner of doing this, are at least similar to, if not the same as, the importance and manner of doing that were explained above regarding the inner surfaces 58, 72 of the air sampler 10's cyclonic cup 14, and thus need not be repeated here.

After the air has passed through the cyclonic cups's air chamber 76a, the air, from which most, if not all, of the target material and the target material carrying water fog particles 54a have been stripped, may then be expelled out through the cyclonic cup's air outlet tube 136.

A sample of the water from the reservoir 53a, which may carry the target material that was stripped from the air, may then be delivered to the detection apparatus 67a after one, or more, trips through the air inlet section 12a and the main body 11a. Fresh water may be added to the air inlet section 12a and the main body 11a from the container valve when shut off, may consume a very small amount of electric power due to its innovative design, and may be long-lived, self-priming, easily cleaned, light-weight, insensitive to shock, and/or computer-controllable.

The peristaltic pump 110 may comprise any suitable motor 112, such as an electric motor, having a drive shaft 114. The peristaltic pump 110 may further comprise a rotor 116 driven by the drive shaft 114; a pair of low friction rollers 118, 120, such as ball bearing rollers, each mounted to the rotor 116 by a respective axle 122, a pair of washers 124, and a pair of C-rings 126; a pump tube 128 mounted in a dual-level raceway 184, and having an input end 190 and an output end 192; and a housing 130, in which the raceway 184 may be mounted so that it may not rotate with respect to the housing 130, and to which the motor 112 may be fixedly mounted in any suitable way, such as by the use of pins or fasteners (not illustrated, for clarity).

Two rollers 118, 120 may be preferred, as providing an acceptable pumping action while preventing undesired back-flow from the pump tube 128's output end 192 for all positions of the rollers 118, 120. However, fewer, or more, rollers 118, 120 may be used. Although two rollers 118, 120 may not provide as smooth a flow of fluid as a pump 110 having more rollers 118, 120, this may be acceptable for the air samplers 10, 130, 200 of FIGS. 1, 9, and 12, since they may not require a smoother flow of fluid for proper operation of their sample and/or waste pumps 75, 75b, and 79.

Figure 14:
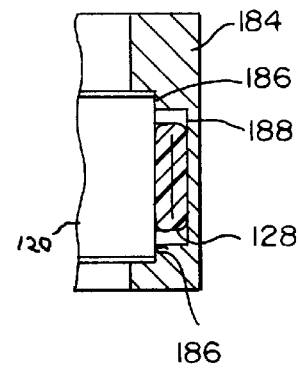
FIG. 14 is a fragmentary, cross-sectional view of a portion of the peristaltic pump 110.
Figure 15:
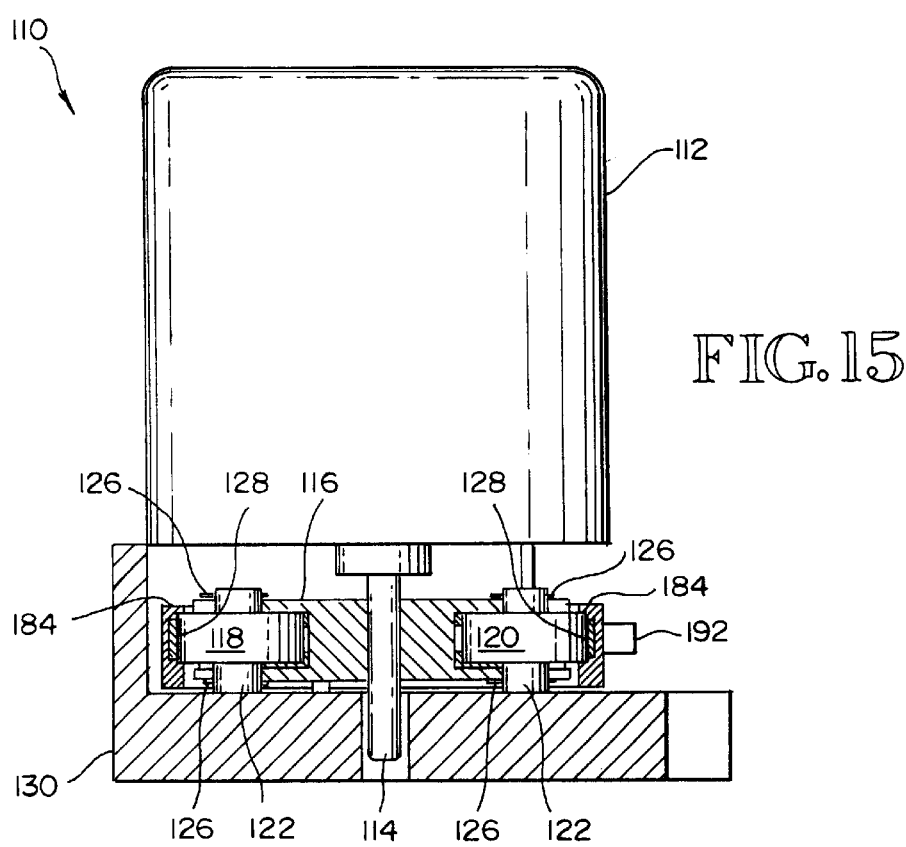
FIG. 15 is a diagrammatic, side elevational view, partly in cross-section, of the peristaltic pump 110.
Figure 16:
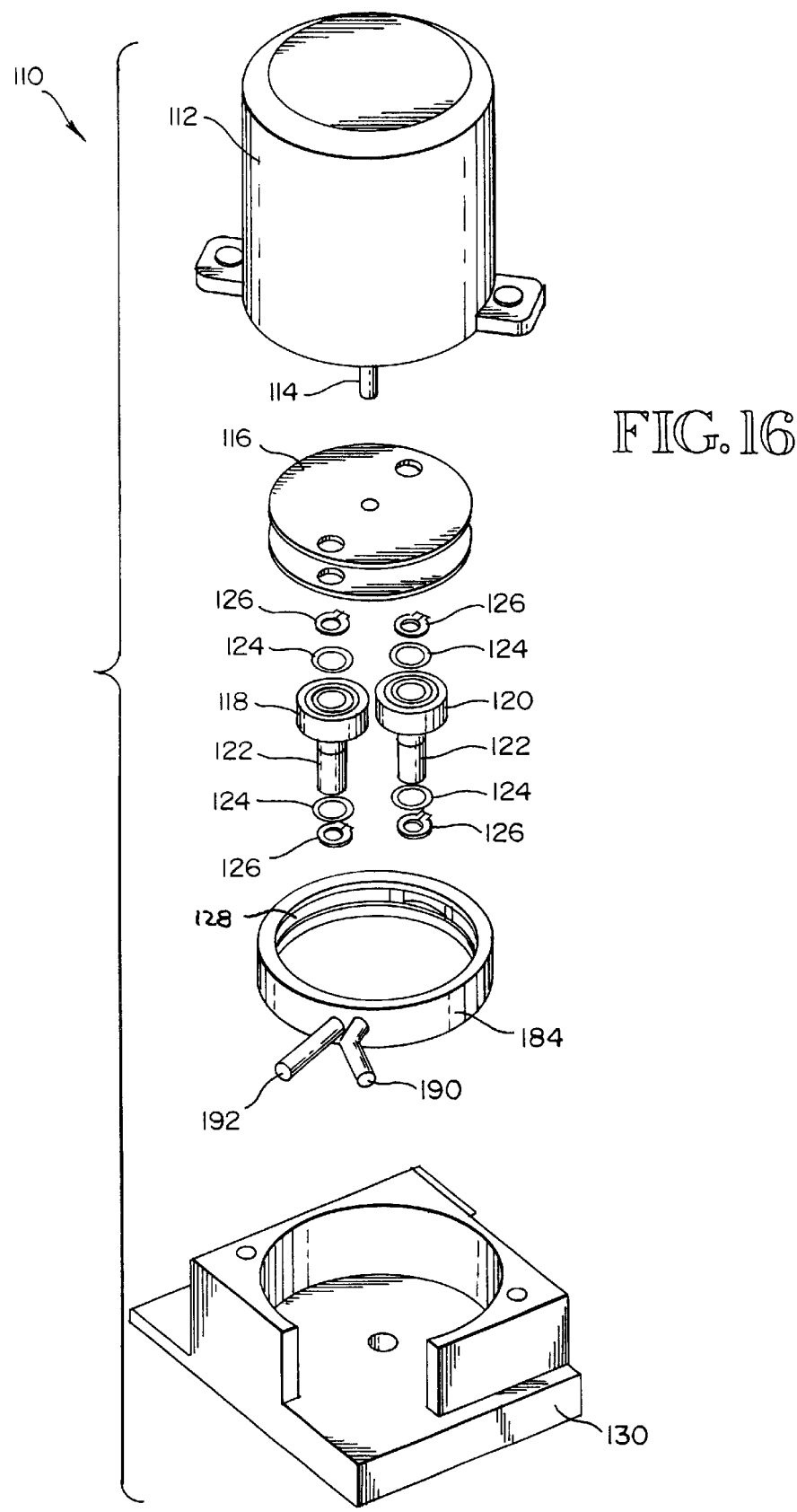
FIG. 16 is a diagrammatic, exploded perspective view of the peristaltic pump 110.

As best seen in FIG. 14, the dual-level raceway 184 comprises an inner circumferential track 186 for the rollers 118, 120; and an outer circumferential track 188 for the pump tube 128. The internal diameter of the raceway 184 may be somewhat smaller than the nominal distance between the outer surfaces of the two rollers 118, 120, so that when the raceway 184 is squeezed laterally and slipped over the rollers 118, 120, the raceway 184 may act as a circular spring, pinching the pump tube 128 shut at the two diametrically opposed contact points between the rollers 118, 120 and the pump tube 128, and may assume a partially elliptical profile.

The raceway 184 may be made from any suitable material, such as metal or plastic; and may be a simple, force-balanced symmetric structure with well understood elastic properties. The stiffness of the raceway 184 may be selected so that the requirements for the pinch-off force for the pump tube 128 and the pressure output from the pump tube 128 may be met without generating excessive mechanical loading that may waste input power to the pump 110.

An elastic raceway 184 may be used since it may allow the realization of a pump 110 comprising only two rollers 118, 120, without concern that the load on the pump tube 128 may vary from point-to-point around the circumference of the raceway 184. In comparison, a conventional 180° wide, spring-loaded peristaltic pump approach may require that its conventional raceway be split into two 90° pieces, so that the desired radial loading and tubing compression can be approximated.

Alternatively, a relatively non-elastic raceway 184 may be used. In such an event, the rollers 118, 120 may be covered with an elastic material that may be selected to be stiff enough to provide the requisite squeezing force on the pump tube 128. Alternatively, the rollers 118, 120 may be spring mounted in the rotor 116, so they exert the desired, springy, outward force against the pump tube 128.

During operation of the pump 110, the rollers 118, 120 pinch the pump tube 128 shut against the raceway 184 as they roll around the raceway 184; thereby automatically forcing fluid in the pump tube 128 out of the pump tube's output end 190, while simultaneously drawing fluid into the pump tube's input end 192.

The raceway 184 may provide almost 360° of contact between the rollers 118, 120 and the pump tube 128, thereby providing a maximized length flow stroke of nearly 360° for each of the rollers 118, 120. Such a long flow stroke for the rollers 118, 120 may minimize wear on the pump tube 128, since as the angular field of the raceway 184 is increased, the amount of roller action per unit tube length may be reduced for any give output flow.

The novel design of the pump 110 may help to minimize its power consumption, size and weight because, for example: (a) the rollers 118, 120 may be very low friction ball bearing rollers, as compared to relatively higher friction sleeve bearing rollers; (b) two rollers 118, 120 will require less power to drive, as compared to a pump 110 having more rollers 118, 120; and/or (c) the output pressure from the pump 110 needed for the air samplers 10, 130 and 200 of FIGS. 1, 9 and 12, respectively may be on the order of only a few pounds per square inch, thereby requiring less power to produce, as compared to a pump 120 needed to produce a comparatively higher pressure.

Due to the dual pinch provided for the pump tubing 128 by the two rollers 118, 120, the light weight of the raceway 128, and the elastic nature of the pump tubing 128 and the raceway 128, the pump 110 may be very shock and vibration resistant, and may not leak under either large shock loads or heavy vibration. The pump tubing 128 may be easily cleaned, since it may be smooth-bored; and may be self-priming, due to the sealing nature of each pinch-point on the pump tubing 128 between the rollers 118, 120 and the raceway 128.

By way of non-limiting example, the pump 110 may have the following specifications. The motor 112 may be a miniature DC gear motor, part number A41,865, operated at about 30 RPM and available from Edmund Scientific of Barrington, N.J. The pump tube 128 may be silicone tubing having a 0.074 inch ID (inner diameter), and a 0.125 OD (outer diameter), and may be obtained from Beere Precision Silicone of Racine, Wisconsin. The raceway 184 may be made of any suitable engineering polymer, such as acetals, polyimides, and acrylonitrile butadiene styrene, that is not operated beyond its elastic limit. The raceway 184 may have an OD of about 1.74 inches, an ID of about 1.58 inches, a maximum width between its end faces of about 0.32 inches, and a weight of about 4.0 grams. The rollers 118, 120 may have an OD of about 0.5 inches, and may be ball bearing assemblies purchased from Stock Drive Products of New Hyde Park, N.Y. Intentional interference between the rollers 118, 120 and the ID of the raceway 184 may result in a total elastic deflection of the raceway (once it is assembled onto the rotors 118, 120), of about 0.02 to 0.04 inches. The pump 110 may have a nominal flow of about 12 cc/min, a static pressure capability of about 15 psig, and a total electrical power consumption of about only 0.18 watts. This power consumption may be a factor of about 10 to 20 times less power than that required by a typical "low power" commercial peristaltic pump.

It is understood that the all of the foregoing forms of the invention were described and/or illustrated strictly by way of non-limiting example.

In view of all of the disclosures herein, these and further modifications, adaptations and variations of the present invention will now be apparent to those skilled in the art to which it pertains, within the scope of the following claims.

What is claimed is:

1. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber; and wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means.

2. The air sampler according to claim 1, wherein said main body comprises a cyclonic cup; wherein said main body air vortex comprises a cyclonic cup air vortex located within said cyclonic cup; wherein said main body further comprises a passive stripping liquid fog generating means that is in fluid communication with said liquid inlet means; wherein at least part of said passive stripping liquid fog generating means is located within said cyclonic cup air vortex; wherein said passive stripping liquid fog generating means is for generating fog particles from said stripping liquid and said cyclonic cup air vortex; wherein said fog particles strip a fog-stripped part of said target material from said main body air vortex; wherein said main body air vortex deposits on said stripping portion of said main body inner surface at least some of said fog particles; wherein said fog particles that are deposited on said stripping portion of said main body inner surface comprise at least part of said thin liquid film on said stripping portion of said main body inner surface; and wherein said fog-stripped part of said target material comprises at least part of said film-stripped part of said target material.

3. The air sampler according to claim 1, wherein said one integrally formed piece is selected from the group consisting of one integrally formed blow-molded piece and one integrally formed roto-molded piece.

4. The air sampler according to claim 1, wherein said air sampler further comprises a fan means for creating said air flow.

5. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said air sampler further comprises a peristaltic pump means for removing at least some of said stripping liquid from said liquid outlet means; wherein said peristaltic pump means comprises a rotor; at least one roller carried by said rotor; a driving means for urging said rotor to rotate; a raceway comprising a pump tube track; a pump tube mounted in a said pump tube track; and mounting means for preventing rotation of said raceway with respect to said driving means; and wherein a pinched-shut portion of said pump tube is located between said at least one roller and said pump tube track.

6. The air sampler according to claim 5, wherein said pump tube track defines an arc having an angular size greater than about 280°.

7. The air sampler according to claim 5, wherein said pump tube track defines an arc having an angular size greater than about 350° and less than about 360°.

8. The air sampler according to claim 5, wherein said peristaltic pump means comprises only two rollers carried by said rotor; and wherein a respective said pinched-shut portion of said pump tube is located between each of said two rollers and said pump tube track.

9. The air sampler according to claim 5, wherein said raceway further comprises a roller track for said at least one roller; wherein said roller track has a bottom; and wherein said pump tube track is located in said bottom of said roller track.

10. The air sampler according to claim 5, wherein said raceway has an elasticity and a size that are selected to enable said raceway to help said at least one roller to pinch shut said pump tube between said at least one roller and said pump tube track.

11. The air sampler according to claim 10, wherein said raceway is selected to be effectively inelastic; and wherein said at least one roller comprises an resilient outer surface having a thickness and a resiliency selected to enable said at least one roller to pinch shut said pump tube against said pump tube track.

12. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said target material has an effective partition coefficient in said stripping liquid; and wherein said stripping liquid comprises a binding material that is selected to increase said effective partition coefficient of said target material in said stripping liquid.

13. The air sampler according to claim 12, wherein said binding material comprises an antibody.

14. The air sampler according to claim 12, wherein said binding material comprises particles of a polymerized hydroxyethyl methacrylate that was polymerized in the presence of said target material.

15. The air sampler according to claim 12, wherein said binding material comprises a protein.

16. The air sampler according to claim 15, wherein said target material comprises a triazine class of pesticide.

17. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said air sampler further comprises recycling means for conveying said stripping liquid and said film-stripped part of said target material at least once from said liquid outlet means to said liquid inlet means; and wherein each time said stripping liquid passes from said liquid inlet means to said liquid outlet means said stripping liquid strips an additional said film-stripped part of said target material from said main body air vortex, to increase the concentration of said film-stripped part of said target material in said stripping liquid.

18. The air sampler according to claim 17, wherein said liquid outlet means is located higher than said liquid inlet means a distance that is selected to permit said stripping liquid to be gravity fed from said liquid outlet means to said liquid inlet means.

19. The air sampler according to claim 17, wherein said main body air vortex creates a low pressure area in a central part of said main body air vortex; wherein said liquid inlet means comprises a liquid inlet port; and wherein said liquid inlet port is located in said low pressure area; and wherein said low pressure area aspirates said stripping liquid into said main body through said liquid inlet port.

20. An air sampler; wherein said air sampler is adapted to strip a target material from an air flow with a stripping liquid; wherein said air sampler comprises:

a main body means comprising a main body, a main body inner surface and a main body air chamber, wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein, in a given period of time, a certain volume of said air flow and a certain volume of said stripping liquid pass through said main body air chamber; and wherein the ratio of said certain volume of said air flow to said certain volume of said stripping liquid is at least about 10,000:1.

21. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein, in a given period of time, a certain volume of said air flow passes through said main body air chamber; wherein a certain volume of said stripping liquid resides in said main body air chamber during said given period of time; and wherein the ratio of said certain volume of said air to said certain volume of said stripping liquid is at least about 10,000:1.

22. An air sampler; wherein said air sampler is adapted to strip a taraet material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises a cyclonic cup; wherein said main body air vortex comprises a cyclonic cup air vortex located within said cyclonic cup; wherein said main body further comprises a passive stripping liquid fog generating means that is in fluid communication with said liquid inlet means; wherein at least part of said passive stripping liquid fog generating means is located within said cyclonic cup air vortex; wherein said passive stripping liquid fog generating means is for generating fog particles from said stripping liquid and said cyclonic cup air vortex; wherein said fog particles strip a fog-stripped part of said target material from said main body air vortex; wherein said main body air vortex deposits on said stripping portion of said main body inner surface at least some of said fog particles; wherein said fog particles that are deposited on said stripping portion of said main body inner surface comprise at least part of said thin liquid film on said stripping portion of said main body inner surface; wherein said fog-stripped part of said target material comprises at least part of said film-stripped part of said target material; and wherein said passive stripping liquid fog generating means comprises a passive spiral fog generating nozzle.

23. The air sampler according to claim 22, wherein said cyclonic cup comprises a cyclonic cup base; wherein said cyclonic cup has a height measured from said cyclonic cup base; wherein said passive spiral fog generating nozzle has a height measured from said cyclonic cup base; and wherein the ratio of said height of said passive spiral fog generating nozzle to said height of said cyclonic cup is in the range of about 0.5 to 1.0.

24. The air sampler according to claim 22, wherein said passive spiral fog generating nozzle comprises a nozzle base and a nozzle free end; and wherein said passive spiral fog generating nozzle is at least generally tapered from said nozzle base to said nozzle free end.

25. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber: an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises a cyclonic cup; wherein said main body air vortex comprises a cyclonic cup air vortex located within said cyclonic cup; wherein said main body further comprises a passive stripping liquid fog generating means that is in fluid communication with said liquid inlet means; wherein at least part of said passive stripping liquid fog generating means is located within said cyclonic cup air vortex; wherein said passive stripping liquid fog generating means is for generating fog particles from said stripping liquid and said cyclonic cup air vortex; wherein said fog particles strip a fog-stripped part of said target material from said main body air vortex; wherein said main body air vortex deposits on said stripping portion of said main body inner surface at least some of said fog particles; wherein said fog particles that are deposited on said stripping portion of said main body inner surface comprise at least part of said thin liquid film on said stripping portion of said main body inner surface; wherein said fog-stripped part of said target material comprises at least part of said film-stripped part of said target material;

wherein said air sampler further comprises recycling means for conveying said stripping liquid and said film-stripped part of said target material at least once from said liquid outlet means to said liquid inlet means; and wherein each time said stripping liquid passes from said liquid inlet means to said liquid outlet means said stripping liquid strips an additional said fog-stripped part of said target material and strips an additional said film-stripped part of said target material, to increase the concentration of said fog-stripped part of said target material and said film-stripped part of said target material in said stripping liquid.

26. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body further comprises at least one groove in said stripping portion of said main body inner surface; and wherein said at least one groove follows an at least generally spiral path on said stripping portion of said main body inner surface, for at least part of the way between said liquid inlet means and said liquid outlet means.

27. An air sampler; wherein said air sampler is adapted to strip a target material from an air flow with a stripping liquid; wherein said air sampler comprises: a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber: an air outlet means for permitting said air flow to exit said main body air chamber; a liquid inlet means for Permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises reservoir means for collecting said stripping liquid and said film-stripped part of said target material from said stripping portion of said main body inner surface; wherein said liquid outlet means is also for permitting said stripping liquid and said film-stripped part of said target material to exit said main body air chamber through said reservoir means;

wherein said main body further comprises a demister; wherein said demister comprises a demister base and a demister sidewall; wherein said main body air vortex comprises a demister air vortex; wherein said reservoir means is defined by said demister air vortex, said demister base, and said demister sidewall;

wherein said demister sidewall and said demister base each comprises a respective radially enlarged portion;

and wherein said reservoir means is defined by said demister air vortex and said radially enlarged portions of said demister sidewall and said demister base.

28. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises reservoir means for collecting said stripping liquid and said film-stripped part of said target material from said stripping portion of said main body inner surface; and wherein said liquid outlet means is also for permitting said stripping liquid and said film-stripped part of said target material to exit said main body air chamber through said reservoir means;

wherein said main body means further comprises liquid level detection means for detecting the amount of stripping liquid held by said main body means; wherein said main body further comprises a liquid return conduit extending from said reservoir means to said liquid inlet means; and wherein said liquid level detection means comprise means for detecting the passages of bubbles through said liquid return conduit.

29. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises reservoir means for collecting said stripping liquid and said film-stripped part of said target material from said stripping portion of said main body inner surface; and wherein said liquid outlet means is also for permitting said stripping liquid and said film-stripped part of said target material to exit said main body air chamber through said reservoir means;

wherein said main body further comprises a demister; and wherein said demister further comprises a vertically extending gutter means for collecting a portion of said stripping liquid.

30. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises a cyclonic cup, a stripping column and a demister;

wherein said main body air chamber comprises a cyclonic cup air chamber, a stripping column air chamber, and a demister air chamber;

wherein said air inlet means is for permitting said air flow to enter said cyclonic cup air chamber; wherein said air outlet means is for permitting said air flow to exit said demister air chamber; wherein said liquid inlet means is for permitting said stripping liquid to enter said cyclonic cup air chamber; wherein said liquid outlet means is for permitting said stripping liquid to exit said demister air chamber;

wherein said air flow from said air inlet means to said air outlet means passes sequentially through said cyclonic cup, said stripping column, and said demister;

wherein said main body air vortex comprises a cyclonic cup air vortex in said cyclonic cup air chamber, a stripping column air vortex in said stripping column air chamber, and a demister air vortex in said demister air chamber;

wherein said stripping portion of said main body inner surface comprises a cyclonic cup stripping surface and a stripping column stripping surface, wherein said thin liquid film passes sequentially over said cyclonic cup stripping surface and said stripping column stripping surface;

wherein said air sampler further comprises recycling means for conveying said stripping liquid and said film-stripped part of said target material at least once from said liquid outlet means to said liquid inlet means; and wherein each time said stripping liquid passes from said liquid inlet means to said liquid outlet means said stripping liquid strips an additional said film-stripped part of said target material from said cyclonic cup air vortex, said stripping column air vortex and said demister air vortex, to increase the concentration of said film-stripped part of said target material in said stripping liquid.

31. An air sampler; wherein said air sampler is adapted to strip, a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said air inlet means comprises an air inlet tube and an air inlet tube air chamber; wherein said air flow passes through said air inlet tube air chamber during operation of said air sampler; wherein said liquid inlet means comprises a fog generator means located at least partially in said air inlet tube air chamber; wherein said liquid inlet means is also for permitting at least part of said stripping liquid to enter said main body air chamber through said fog generator means and said air inlet tube;

wherein, during operation of said air sampler, said fog generator means is for generating fog particles within said air inlet tube air chamber from said stripping liquid; wherein said air flow passing through said air inlet tube air chamber carries said fog particles from said fog generator means into said main body air chamber; wherein said fog particles strip a fog-stripped part of said target material from said air flow passing through said air inlet tube air chamber and from said main body air vortex;

wherein said main body air vortex deposits on said stripping portion of said main body inner surface at least some of said fog particles; wherein said fog particles that are deposited on said stripping portion of said main body inner surface comprise at least part of said thin liquid film on said stripping portion of said main body inner surface; and wherein said fog-stripped part of said target material comprises at least part of said film-stripped part of said target material.

32. The air sampler according to claim 31, wherein said liquid inlet means is also for permitting at least part of said stripping liquid to directly enter said main body air chamber.

33. The air sampler according to claim 31, wherein said air sampler further comprises recycling means for conveying said stripping liquid and said film-stripped part of said target material at least once from said liquid outlet means to said liquid inlet means; and wherein each time said stripping liquid passes from said liquid inlet means to said liquid outlet means said stripping liquid strips an additional said fog-stripped part of said target material and strips an additional said film-stripped part of said target material, to increase the concentration of said fog-stripped part of said target material and said film-stripped part of said target material in said stripping liquid.

34. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said tar et material from said main body air vortex, and wherein said velocity of said main body air vortex is also selected to enable said main body air vortex to urge said thin liquid film and said film-stripped part of said target material to flow to said liquid outlet means; and wherein said air sampler further comprises constant volume means for recycling said stripping liquid through said main body at least once, and for maintaining a constant volume of said stripping liquid in said main body within a pre-determined lower limit and a predetermined upper limit during operation of said air sampler.

35. The air sampler according to claim 34, wherein said constant volume means comprises a main body stripping liquid reservoir; an output recycling means for conveying said stripping liquid from said main body stripping liquid reservoir to said liquid inlet means; a fresh stripping liquid reservoir for fresh stripping liquid; a fresh stripping liquid output means for delivering said fresh stripping liquid from said fresh stripping liquid reservoir to said main body; and liquid level control means for sensing when said constant volume of said stripping liquid in said main body falls outside said pre-determined lower and upper limits, and for controlling a flow of said fresh stripping liquid through said fresh stripping liquid output means to maintain said constant volume of said stripping liquid in said main body within said pre-determined lower and upper limits.

36. The air sampler according to claim 35, wherein said liquid level control means comprises a float-type liquid level control means for sensing a level of said stripping liquid in said main body stripping liquid reservoir.

37. The air sampler according to claim 35, wherein said liquid level control means comprises a bubble detector-type liquid level control means for sensing the passage of a flow of bubbles through said output recycling means.

38. The air sampler according to claim 35, wherein said liquid level control means comprises a pressure gauge-type liquid level control means for sensing a pressure of said stripping liquid in at least one of said main body stripping liquid reservoir and said output recycling means.

39. The air sampler according to claim 35, wherein said liquid level control means comprises a heated element placed in said stripping liquid in said output recycling means; and wherein said liquid level control means further comprises a temperature-type liquid level control means for sensing a temperature of said heated element.

40. The air sampler according to claim 35, wherein said liquid level control means comprises a velocity-type liquid level control means for sensing at least one of a velocity of said stripping liquid in said output recycling means and a velocity of a flow of particles carried by said stripping liquid in said output recycling means.

41. The air sampler according to claim 35, wherein said liquid level control means comprises an acoustic impedance-type liquid level control means for sensing changes in an acoustic impedance of said stripping liquid in said output recycling means.

42. The air sampler according to claim 35, wherein said liquid level control means comprises an acoustic sensor-type liquid level control means for sensing a turbulence noise of said stripping liquid in said output recycling means.

43. The air sampler according to claim 35, wherein said liquid level control means comprises a stripping liquid film detector-type liquid level control means for sensing said thin liquid film on said stripping portion of said main body inner surface.

44. The air sampler according to claim 43, wherein said stripping liquid film detector-type liquid level control means is selected from the group consisting of: (a) an optical waveguide-type liquid level control means for sensing a series of optical waveguide changes in an at least partially transparent wall of said main body, (b) an acoustic echo-type liquid level control means, (c) a heated wire temperature detecting-type liquid level control means for sensing a temperature of a heated wire in said thin liquid film, and (d) an electromagnetic coupling-type liquid level control means for sensing an electromagnetic coupling of said thin liquid film.

45. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means; and wherein said stripping liquid comprises a surfactant.

46. The air sampler according to claim 45, wherein said surfactant comprises a non-foaming surfactant.

47. The air sampler according to claim 46, wherein said non-foaming surfactant comprises a surfactant that is selected from the group consisting essentially of 2,4,7,9-tetramethyl-5-decyne-4,7-diol ethoxylate (10); 2,4,7,9-tetramethyl-5-decyne-4,7-diol ethoxylate (30); sodium dioctylsulfosuccinate; and p-(nonylphenoxy)poly(glycidol).

48. The air sampler according to claim 45, wherein said target material comprises hydrophobic molecules; wherein said hydrophobic molecules have a solubilization in said stripping liquid; and wherein said surfactant comprises a solubilization surfactant that increases said solubilization of said hydrophobic molecules in said stripping liquid.

49. The air sampler according to claim 48, wherein said solubilization surfactant comprises a surfactant that is selected from the group consisting essentially of: 2,4,7,9-tetramethyl-5-decyne-4,7-diolethoxylate (10)); 2,4,7,9-tetramethyl-5-decyne-4,7-diol ethoxylate (30)); sodium dioctylsulfosuccinate; and p-(nonylphenoxy)poly(glycidol).

50. An air sampler; wherein said air sampler is adapted to strip a target material from an air flow with a stripping liquid; wherein said air sampler comprises:

a main body means comprising a main body a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said tripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means; and wherein at least part of said stripping portion of said main body inner surface comprises a hydrophilic material, to aid in the formation of said thin liquid film on said stripping portion of said main body inner surface.

51. The air sampler according to claim 50, wherein said hydrophilic material comprises a substance selected from the group consisting of a continuously graded junction of said hydrophilic material, a cellulosic material, a hydroxylated material, an etched material, an anodized material, and a roughened material.

52. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises a cyclonic cup; wherein said main body air vortex comprises a cyclonic cup air vortex located within said cyclonic cup; wherein said main body further comprises a passive stripping liquid fog generating means that is in fluid communication with said liquid inlet means; wherein at least part of said passive stripping liquid fog generating means is located within said cyclonic cup air vortex; wherein said passive stripping liquid fog generating means is for generating fog particles from said stripping liquid and said cyclonic cup air vortex; wherein said fog particles strip a fog-stripped part of said target material from said main body air vortex; wherein said main body air vortex deposits on said stripping portion of said main body inner surface at least some of said fog particles; wherein said fog particles that are deposited on said stripping portion of said main body inner surface comprise at least part of said thin liquid film on said stripping portion of said main body inner surface; wherein said fog-stripped part of said target material comprises at least part of said film-stripped part of said target material; and wherein said passive stripping liquid fog generating means comprises a passive fog generating slot.

53. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises a cyclonic cup, a stripping column and a demister; and wherein said cyclonic cup, said stripping column and said demister comprise one integrally formed piece.

54. The air sampler according to claim 53, wherein said air inlet means comprises an air inlet tube; and wherein said one integrally formed piece further comprises said air inlet tube.

55. The air sampler according to claim 54, wherein said one integrally formed piece is selected from the group consisting of one integrally formed blow-molded piece and one integrally formed roto-molded piece.

56. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises a cyclonic cup, a stripping column and a demister; wherein said cyclonic cup, said stripping column and said demister each comprise respective intersecting surfaces; and wherein at least some of said respective intersecting surfaces are joined by a respective smoothly curved fillet.

57. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises reservoir means for collecting said stripping liquid and said film-stripped part of said target material from said stripping portion of said main body inner surface; and wherein said liquid outlet means is also for permitting said stripping liquid and said film-stripped part of said target material to exit said main body air chamber through said reservoir means.

58. The air sampler according to claim 57, wherein said main body further comprises a demister; wherein said demister comprises a demister base and a demister sidewall; wherein said main body air vortex comprises a demister air vortex; and wherein said reservoir means is defined by said demister air vortex, said demister base, and said demister sidewall.

59. The air sampler according to claim 57, wherein said main body means further comprises liquid level detection means for detecting the amount of stripping liquid held by said reservoir means; and wherein said liquid level detection means comprise a float located in said reservoir means and a pair of vertically separated float detector means for detecting the elevation of said float.

60. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein, in a given period of time, a certain volume of said air flow passes through said main body air chamber; wherein a certain volume of said stripping liquid resides in said main body air chamber during said given period of time; and wherein the ratio of said certain volume of said air to said certain volume of said stripping liquid is at least about 10,000:1.

61. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means; and wherein said air sampler is adapted to create said air flow by a ram air effect at said air inlet means, due to a relative motion between said air inlet means and an air mass to be sampled.

62. The air sampler according to claim 61, wherein said air inlet means comprises an air inlet tube and an air scoop for said air inlet tube; and wherein a cross-sectional area of an inlet of said air scoop is larger than a cross-sectional area of said air inlet tube.

63. An air sampler; wherein said air sampler is adapted to strip a target material from an air flow with a stripping liquid; wherein said air sampler comprises:

a main body means comprising a main body, a main body inner surface and a main body air chamber; wherein said main body inner surface defines said main body air chamber; wherein said main body air chamber is located within said main body;

wherein said air sampler further comprises an air inlet means for permitting said air flow to enter said main body air chamber; an air outlet means for permitting said air flow to exit said main body air chamber; a liquid inlet means for permitting said stripping liquid to enter said main body air chamber; a liquid outlet means for permitting said stripping liquid to exit said main body air chamber;

wherein, during operation of said air sampler, said main body means is for forming said air flow from said air inlet means into a main body air vortex within said main body air chamber, wherein said main body air vortex has a velocity with respect to a stripping portion of said main body inner surface that is selected to enable said main body air vortex to urge said stripping liquid from said liquid inlet means to form a thin liquid film on said stripping portion of said main body inner surface, wherein said thin liquid film strips a film-stripped part of said target material from said main body air vortex, and wherein said velocity of said main body air vortex is also selected to enable said main body air vortex to urge said thin liquid film and said film-stripped part of said target material to flow to said liquid outlet means;

wherein said main body comprises a cyclonic cup, a stripping column and a demister;

wherein said main body air chamber comprises a cyclonic cup air chamber, a stripping column air chamber, and a demister air chamber;

wherein said air inlet means is for permitting said air flow to enter said cyclonic cup air chamber; wherein said air outlet means is for permitting said air flow to exit said demister air chamber; wherein said liquid inlet means is for permitting said stripping liquid to enter said cyclonic cup air chamber; wherein said liquid outlet means is for permitting said stripping liquid to exit said demister air chamber;

wherein said air flow from said air inlet means to said air outlet means passes sequentially through said cyclonic cup, said stripping column, and said demister;

wherein said main body air vortex comprises a cyclonic cup air vortex in said cyclonic cup air chamber, a stripping column air vortex in said stripping column air chamber, and a demister air vortex in said demister air chamber;

wherein said stripping portion of said main body inner surface comprises a cyclonic cup stripping surface and a stripping column stripping surface; and wherein said thin liquid film passes sequentially over said cyclonic cup stripping surface and said stripping column stripping surface.

64. The air sampler according to claim 63, wherein said stripping column air chamber has a cross-sectional area smaller than a cross-sectional area of said cyclonic cur air chamber; wherein said stripping column air vortex rotates faster than said cyclonic cup air vortex, to create a relatively lower pressure area in said stripping column air chamber, to permit a relatively higher pressure in said cyclonic cup air chamber to urge said thin liquid film from said cyclonic cup stripping surface to said stripping column stripping surface.

65. The air sampler according to claim 64, wherein said demister comprises a reservoir means for collecting said stripping liquid and said film-stripped part of said target material from said cyclonic cup stripping surface, said stripping column stripping surface, and said demister stripping surface; and wherein said liquid outlet means is also for permitting said stripping liquid and said film-stripped part of said target material to exit said demister air chamber through said reservoir means.

66. The air sampler according to claim 65, wherein said demister air chamber has a cross-sectional area that is larger than a cross-sectional area of said stripping column air chamber;

wherein said cross-sectional area of said demister air chamber is selected to permit said air flow to travel through said demister air chamber at a velocity that is slow enough to enable said air flow through said demister air chamber to drop at least part of any stripping liquid that was air-entrained in said air flow in said cyclonic cup air chamber and in said stripping column air chamber;

wherein said demister comprises a demister sidewall and a demister base; wherein a demister portion of said stripping column extends through said demister base into said demister air chamber; and wherein said reservoir means is defined between said demister base, said demister sidewall and said demister portion of said stripping column.

67. The air sampler according to claim 1, wherein said liquid inlet means is also for permitting at least part of said stripping liquid to directly enter said main body air chamber.

* * * * *

UNITED STATES PATENT AND TRADEMARK OFFICE
CERTIFICATE OF CORRECTION

PATENT NO.    : 6,532,835 B1
DATED         : March 18, 2003
INVENTOR(S)   : Elric W. Saaski, Chuck C. Jung and David A. McCrae It is certified that error appears in the above-identified patent and that said Letters Patent is hereby corrected as shown below:

Column 47,
Line 55, the claim reference numeral "1" should read -- 53 --.

Column 64,
Line 31, cancel beginning with "60. An air sampler" to and including "about 10,000:1"

Column 65,
Line 3, insert the following claim:
      60. The air sampler according to claim 57, wherein said main body further comprises a stripping column and a demister; wherein a reservoir portion of said stripping column extends into said demister; and wherein said reservoir means is defined by a reservoir portion of said demister and said reservoir of said stripping column.

Column 66,
Line 48, the claim reference numeral "64" should read -- 63 --.

Signed and Sealed this

Eleventh Day of May, 2004

JON W. DUDAS
*Acting Director of the United States Patent and Trademark Office*